(12) United States Patent
McDermott et al.

(10) Patent No.: US 11,598,664 B2
(45) Date of Patent: Mar. 7, 2023

(54) INJECTOR PRESSURE CALIBRATION SYSTEM AND METHOD

(71) Applicant: BAYER HEALTHCARE LLC, Whippany, NJ (US)

(72) Inventors: Michael McDermott, Pittsburgh, PA (US); Chelsea Marsh, Pittsburgh, PA (US); Michael Spohn, Fenelton, PA (US); William Barone, Pittsburgh, PA (US); Robert Praniewicz, New Kensington, PA (US); Edden Rabin, Wexford, PA (US); Corey Savannah, Butler, PA (US); Vince Delbrugge, Indiana, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 544 days.

(21) Appl. No.: 16/621,784

(22) PCT Filed: Aug. 28, 2018

(86) PCT No.: PCT/US2018/048313
§ 371 (c)(1),
(2) Date: Dec. 12, 2019

(87) PCT Pub. No.: WO2019/046282
PCT Pub. Date: Mar. 7, 2019

(65) Prior Publication Data
US 2020/0149948 A1    May 14, 2020

Related U.S. Application Data

(60) Provisional application No. 62/552,428, filed on Aug. 31, 2017.

(51) Int. Cl.
*G01F 25/17* (2022.01)
*A61M 5/20* (2006.01)
(Continued)

(52) U.S. Cl.
CPC ............... *G01F 25/17* (2022.01); *A61M 5/20* (2013.01); *F16K 37/0083* (2013.01); *G05D 15/01* (2013.01)

(58) Field of Classification Search
CPC ........... G01F 25/17; A61M 5/20; G05D 15/01
(Continued)

(56) References Cited

U.S. PATENT DOCUMENTS

| 383,858 A | 6/1888 | Campbell |
| 508,584 A | 11/1893 | Stevens |

(Continued)

FOREIGN PATENT DOCUMENTS

| CA | 2045070 A1 | 2/1992 |
| CA | 2077712 A1 | 12/1993 |

(Continued)

OTHER PUBLICATIONS

"International Preliminary Report on Patentability from PCT Application No. PCT/US2018/048313", dated Mar. 12, 2020.

(Continued)

*Primary Examiner* — Md Azad
(74) *Attorney, Agent, or Firm* — David Schramm; Joseph L. Kent; James R. Stevenson

(57) ABSTRACT

A calibration system for calibrating a pressure output of a fluid injector having a housing configured for connecting to the fluid injector; a drive member engagement portion configured for contacting a drive member of the fluid injector; a compressible member, which may have a known modulus of compression, connected at its proximal end to the drive member engagement portion, wherein the compressible member is compressed with movement of the drive member of the fluid injector between a first, uncompressed position and a second, at least partially compressed position of the fluid injector in a distal direction; and a sensor (Continued)

connected to the compressible member is described. The sensor is configured for measuring at least one of a force imparted by the drive member and a displacement of the drive member when the compressible member is in the second, at least partially compressed position. The system may generate a calibration curve for the drive member of the fluid injector and allow the generation of a fault condition. Methods for calibrating a fluid injector are also described.

20 Claims, 10 Drawing Sheets

(51) Int. Cl.
    *F16K 37/00*     (2006.01)
    *G05D 15/01*     (2006.01)

(58) Field of Classification Search
    USPC ........................................................ 73/1, 160
    See application file for complete search history.

(56) References Cited

U.S. PATENT DOCUMENTS

| | | | |
|---|---|---|---|
| 945,143 | A | 1/1910 | Iacques |
| 1,020,166 | A | 3/1912 | Tibbott |
| 2,511,291 | A | 6/1950 | Mueller |
| 2,583,206 | A | 1/1952 | Borck et al. |
| 3,156,236 | A | 11/1964 | Williamson |
| 3,159,312 | A | 12/1964 | Van Sciver, II |
| 3,276,472 | A | 10/1966 | Jinkens et al. |
| 3,349,713 | A | 10/1967 | Fassbender |
| 3,520,295 | A | 7/1970 | Paul |
| 3,523,523 | A | 8/1970 | Heinrich et al. |
| 3,623,474 | A | 11/1971 | Heilman |
| 3,635,444 | A | 1/1972 | Charles |
| 3,671,208 | A | 6/1972 | Wayne |
| 3,701,345 | A | 10/1972 | Heilman |
| 3,719,207 | A | 3/1973 | Takeda |
| 3,755,655 | A | 8/1973 | Senegal |
| 3,793,600 | A | 2/1974 | Grosbard |
| 3,812,843 | A | 5/1974 | Wootten et al. |
| 3,817,843 | A | 6/1974 | Barrett |
| 3,839,708 | A | 10/1974 | Lyons et al. |
| 3,868,967 | A | 3/1975 | Harding |
| 3,888,239 | A | 6/1975 | Rubinstein |
| 3,895,220 | A | 7/1975 | Nelson et al. |
| 3,898,983 | A | 8/1975 | Elam |
| 3,927,955 | A | 12/1975 | Spinosa et al. |
| 3,941,126 | A | 3/1976 | Dietrich et al. |
| 3,958,103 | A | 5/1976 | Oka et al. |
| 3,968,195 | A | 7/1976 | Bishop |
| 3,995,381 | A | 12/1976 | Manfred et al. |
| 4,001,549 | A | 1/1977 | Corwin |
| 4,006,736 | A | 2/1977 | Kranys et al. |
| 4,038,981 | A | 8/1977 | Lefevre et al. |
| 4,044,757 | A | 8/1977 | McWhorter et al. |
| 4,090,502 | A | 5/1978 | Tajika |
| 4,135,247 | A | 1/1979 | Gordon et al. |
| 4,151,845 | A | 5/1979 | Clemens |
| 4,187,057 | A | 2/1980 | Xanthopoulos |
| 4,191,183 | A | 3/1980 | Mendelson |
| 4,199,000 | A | 4/1980 | Edstrom |
| 4,204,775 | A | 5/1980 | Speer |
| 4,207,871 | A | 6/1980 | Jenkins |
| 4,208,136 | A | 6/1980 | King et al. |
| 4,223,675 | A | 9/1980 | Williams |
| 4,262,824 | A | 4/1981 | Hrynewycz |
| 4,263,916 | A | 4/1981 | Brooks et al. |
| 4,280,494 | A | 7/1981 | Cosgrove et al. |
| 4,284,073 | A | 8/1981 | Krause et al. |
| 4,315,247 | A | 2/1982 | Germanton |
| 4,319,568 | A | 3/1982 | Tregoning |
| 4,329,067 | A | 5/1982 | Goudy, Jr. |
| 4,340,153 | A | 7/1982 | Spivey |
| 4,341,153 | A | 7/1982 | Bowser |
| 4,392,847 | A | 7/1983 | Whitney et al. |
| 4,392,849 | A | 7/1983 | Petre et al. |
| 4,396,385 | A | 8/1983 | Kelly et al. |
| 4,402,310 | A | 9/1983 | Kimura |
| 4,409,966 | A | 10/1983 | Lambrecht et al. |
| 4,434,820 | A | 3/1984 | Glass |
| 4,434,822 | A | 3/1984 | Bellamy et al. |
| 4,441,823 | A | 4/1984 | Power et al. |
| 4,444,198 | A | 4/1984 | Petre |
| 4,447,230 | A | 5/1984 | Gula et al. |
| 4,448,200 | A | 5/1984 | Brooks et al. |
| 4,474,476 | A | 10/1984 | Thomsen |
| 4,477,923 | A | 10/1984 | Baumann et al. |
| 4,479,760 | A | 10/1984 | Bilstad et al. |
| 4,479,761 | A | 10/1984 | Bilstad et al. |
| 4,479,762 | A | 10/1984 | Bilstad et al. |
| 4,504,908 | A | 3/1985 | Riederer et al. |
| 4,509,526 | A | 4/1985 | Barnes et al. |
| 4,512,764 | A | 4/1985 | Wunsch |
| 4,542,459 | A | 9/1985 | Riederer |
| 4,544,949 | A | 10/1985 | Kurihara |
| 4,551,133 | A | 11/1985 | Zegers et al. |
| 4,552,130 | A | 11/1985 | Kinoshita |
| 4,559,036 | A | 12/1985 | Wunsch |
| 4,563,175 | A | 1/1986 | Lafond |
| 4,578,802 | A | 3/1986 | Itoh |
| 4,585,009 | A | 4/1986 | Barker et al. |
| 4,585,941 | A | 4/1986 | Bergner |
| 4,610,670 | A | 9/1986 | Spencer |
| 4,610,790 | A | 9/1986 | Reti et al. |
| 4,611,340 | A | 9/1986 | Okazaki |
| 4,612,572 | A | 9/1986 | Komatsu et al. |
| 4,625,494 | A | 12/1986 | Iwatschenko et al. |
| 4,626,144 | A | 12/1986 | Berner |
| 4,633,307 | A | 12/1986 | Honda |
| 4,634,426 | A | 1/1987 | Kamen |
| 4,636,144 | A | 1/1987 | Abe et al. |
| 4,655,197 | A | 4/1987 | Atkinson |
| 4,662,906 | A | 5/1987 | Matkovich et al. |
| 4,672,651 | A | 6/1987 | Horiba et al. |
| 4,676,776 | A | 6/1987 | Howson |
| 4,682,170 | A | 7/1987 | Kubota et al. |
| 4,689,670 | A | 8/1987 | Okazaki |
| 4,710,166 | A | 12/1987 | Thompson et al. |
| 4,723,261 | A | 2/1988 | Janssen et al. |
| 4,750,643 | A | 6/1988 | Wortrich |
| 4,754,786 | A | 7/1988 | Roberts |
| 4,781,687 | A | 11/1988 | Wall |
| 4,783,273 | A | 11/1988 | Knutsson et al. |
| 4,789,014 | A | 12/1988 | DiGianfilippo et al. |
| 4,793,357 | A | 12/1988 | Lindstrom |
| 4,795,429 | A | 1/1989 | Feldstein |
| 4,798,590 | A | 1/1989 | O'Leary et al. |
| 4,804,454 | A | 2/1989 | Asakura et al. |
| 4,823,833 | A | 4/1989 | Hogan et al. |
| 4,835,521 | A | 5/1989 | Andrejasich et al. |
| 4,836,187 | A | 6/1989 | Iwakoshi et al. |
| 4,838,856 | A | 6/1989 | Mulreany et al. |
| 4,840,620 | A | 6/1989 | Kobayashi et al. |
| 4,844,052 | A | 7/1989 | Iwakoshi et al. |
| 4,853,521 | A | 8/1989 | Claeys et al. |
| 4,854,301 | A | 8/1989 | Nakajima |
| 4,854,324 | A | 8/1989 | Hirschman et al. |
| 4,857,056 | A | 8/1989 | Talonn |
| 4,874,359 | A | 10/1989 | White et al. |
| 4,879,880 | A | 11/1989 | Harrison |
| 4,880,014 | A | 11/1989 | Zarowitz et al. |
| 4,887,208 | A | 12/1989 | Schneider et al. |
| 4,887,554 | A | 12/1989 | Whitford |
| 4,901,731 | A | 2/1990 | Millar |
| 4,903,705 | A | 2/1990 | Imamura et al. |
| 4,913,154 | A | 4/1990 | Ermert et al. |
| 4,922,916 | A | 5/1990 | Ermert et al. |
| 4,925,444 | A | 5/1990 | Orkin et al. |
| 4,929,818 | A | 5/1990 | Bradbury et al. |
| 4,935,005 | A | 6/1990 | Haines |
| 4,936,832 | A | 6/1990 | Vaillancourt |
| 4,943,279 | A | 7/1990 | Samiotes et al. |

(56) References Cited

U.S. PATENT DOCUMENTS

| | | | |
|---|---|---|---|
| 4,943,779 | A | 7/1990 | Pedersen et al. |
| 4,943,987 | A | 7/1990 | Asahina et al. |
| 4,946,256 | A | 8/1990 | Woodruff |
| 4,946,439 | A | 8/1990 | Eggers |
| 4,947,412 | A | 8/1990 | Mattson |
| 4,950,245 | A | 8/1990 | Brown et al. |
| 4,952,068 | A | 8/1990 | Flint |
| 4,954,129 | A | 9/1990 | Giuliani et al. |
| 4,965,726 | A | 10/1990 | Heuscher et al. |
| 4,966,579 | A | 10/1990 | Polaschegg |
| 4,976,687 | A | 12/1990 | Martin |
| 4,978,335 | A | 12/1990 | Arthur, III |
| 4,981,467 | A | 1/1991 | Bobo, Jr. et al. |
| 4,995,064 | A | 2/1991 | Wilson et al. |
| 5,002,055 | A | 3/1991 | Merki et al. |
| 5,004,472 | A | 4/1991 | Wallace et al. |
| 5,009,654 | A | 4/1991 | Minshall et al. |
| 5,010,473 | A | 4/1991 | Jacobs |
| 5,013,173 | A | 5/1991 | Shiraishi |
| 5,018,173 | A | 5/1991 | Komai et al. |
| 5,032,112 | A | 7/1991 | Fairchild et al. |
| 5,034,987 | A | 7/1991 | Fujimoto et al. |
| 5,040,537 | A | 8/1991 | Katakura |
| 5,053,002 | A | 10/1991 | Barlow |
| 5,054,044 | A | 10/1991 | Audon et al. |
| 5,056,568 | A | 10/1991 | DiGianfilippo et al. |
| 5,059,171 | A | 10/1991 | Bridge et al. |
| 5,059,173 | A | 10/1991 | Sacco |
| 5,061,243 | A | 10/1991 | Winchell et al. |
| 5,069,662 | A | 12/1991 | Bodden |
| 5,078,683 | A | 1/1992 | Sancoff et al. |
| 5,088,981 | A | 2/1992 | Howson et al. |
| 5,100,380 | A | 3/1992 | Epstein et al. |
| 5,104,374 | A | 4/1992 | Bishko et al. |
| 5,104,387 | A | 4/1992 | Pokorney et al. |
| 5,108,365 | A | 4/1992 | Woods, Jr. |
| 5,111,492 | A | 5/1992 | Klausz |
| 5,113,905 | A | 5/1992 | Pruitt et al. |
| 5,123,056 | A | 6/1992 | Wilson |
| 5,123,121 | A | 6/1992 | Broersma |
| 5,125,018 | A | 6/1992 | Asahina |
| 5,128,121 | A | 7/1992 | Berg et al. |
| 5,133,336 | A | 7/1992 | Savitt et al. |
| 5,135,000 | A | 8/1992 | Akselrod et al. |
| 5,140,862 | A | 8/1992 | Pappalardo |
| 5,150,292 | A | 9/1992 | Hoffmann et al. |
| 5,166,961 | A | 11/1992 | Brunnett et al. |
| 5,180,895 | A | 1/1993 | Briggs et al. |
| 5,180,896 | A | 1/1993 | Gibby et al. |
| 5,190,744 | A | 3/1993 | Rocklage et al. |
| 5,191,878 | A | 3/1993 | Iida et al. |
| 5,196,007 | A | 3/1993 | Ellman et al. |
| 5,199,604 | A | 4/1993 | Palmer et al. |
| 5,207,642 | A | 5/1993 | Orkin et al. |
| 5,215,095 | A | 6/1993 | Macvicar et al. |
| 5,228,070 | A | 7/1993 | Mattson |
| 5,230,614 | A | 7/1993 | Zanger et al. |
| 5,242,390 | A | 9/1993 | Goldrath |
| 5,249,122 | A | 9/1993 | Stritzke |
| 5,249,579 | A | 10/1993 | Hobbs et al. |
| 5,262,946 | A | 11/1993 | Heuscher |
| 5,267,174 | A | 11/1993 | Kaufman et al. |
| 5,269,756 | A | 12/1993 | Dryden |
| 5,273,537 | A | 12/1993 | Haskvitz et al. |
| 5,274,218 | A | 12/1993 | Urata et al. |
| 5,276,614 | A | 1/1994 | Heuscher |
| 5,286,252 | A | 2/1994 | Tuttle et al. |
| 5,287,273 | A | 2/1994 | Kupfer et al. |
| 5,295,967 | A | 3/1994 | Rondelet et al. |
| 5,300,031 | A | 4/1994 | Neer et al. |
| 5,301,656 | A | 4/1994 | Negoro et al. |
| 5,301,672 | A | 4/1994 | Kalender |
| 5,304,126 | A | 4/1994 | Epstein et al. |
| 5,310,997 | A | 5/1994 | Roach et al. |
| 5,311,568 | A | 5/1994 | McKee, Jr. et al. |
| 5,313,992 | A | 5/1994 | Graben |
| 5,317,506 | A | 5/1994 | Coutre et al. |
| 5,328,463 | A | 7/1994 | Barton et al. |
| 5,329,459 | A | 7/1994 | Kaufman et al. |
| 5,334,141 | A | 8/1994 | Carr et al. |
| 5,339,799 | A | 8/1994 | Kami et al. |
| 5,349,625 | A | 9/1994 | Born et al. |
| 5,349,635 | A | 9/1994 | Scott |
| 5,352,979 | A | 10/1994 | Conturo |
| 5,354,273 | A | 10/1994 | Hagen |
| 5,361,761 | A | 11/1994 | Van et al. |
| 5,362,948 | A | 11/1994 | Morimoto |
| 5,368,562 | A | 11/1994 | Blomquist et al. |
| 5,368,567 | A | 11/1994 | Lee |
| 5,368,570 | A | 11/1994 | Thompson et al. |
| 5,373,231 | A | 12/1994 | Boll et al. |
| 5,376,070 | A | 12/1994 | Purvis et al. |
| 5,378,231 | A | 1/1995 | Johnson et al. |
| 5,382,232 | A | 1/1995 | Hague et al. |
| 5,383,231 | A | 1/1995 | Yamagishi |
| 5,383,858 | A | 1/1995 | Reilly et al. |
| 5,385,540 | A | 1/1995 | Abbott et al. |
| 5,388,139 | A | 2/1995 | Beland |
| 5,392,849 | A | 2/1995 | Matsunaga et al. |
| 5,400,792 | A | 3/1995 | Hoebel et al. |
| 5,417,213 | A | 5/1995 | Prince |
| 5,431,627 | A | 7/1995 | Pastrone et al. |
| 5,433,704 | A | 7/1995 | Ross et al. |
| 5,445,621 | A | 8/1995 | Poli et al. |
| 5,450,847 | A | 9/1995 | Kaempfe et al. |
| 5,453,639 | A | 9/1995 | Cronin et al. |
| 5,456,255 | A | 10/1995 | Abe et al. |
| 5,458,128 | A | 10/1995 | Polanyi et al. |
| 5,459,769 | A | 10/1995 | Brown |
| 5,460,609 | A | 10/1995 | O'Donnell |
| 5,464,391 | A | 11/1995 | Devale |
| 5,468,240 | A | 11/1995 | Gentelia et al. |
| 5,469,769 | A | 11/1995 | Sawada et al. |
| 5,469,849 | A | 11/1995 | Sasaki et al. |
| 5,472,403 | A | 12/1995 | Cornacchia et al. |
| 5,474,683 | A | 12/1995 | Bryant et al. |
| 5,485,831 | A | 1/1996 | Holdsworth et al. |
| 5,489,265 | A | 2/1996 | Montalvo et al. |
| 5,494,036 | A | 2/1996 | Uber, III et al. |
| 5,494,822 | A | 2/1996 | Sadri |
| 5,496,273 | A | 3/1996 | Pastrone et al. |
| 5,507,412 | A | 4/1996 | Ebert et al. |
| 5,515,851 | A | 5/1996 | Goldstein |
| 5,522,798 | A | 6/1996 | Johnson et al. |
| 5,531,679 | A | 7/1996 | Schulman et al. |
| 5,531,697 | A | 7/1996 | Olsen et al. |
| 5,533,978 | A | 7/1996 | Teirstein |
| 5,544,215 | A | 8/1996 | Shroy, Jr. et al. |
| 5,547,470 | A | 8/1996 | Johnson et al. |
| 5,552,130 | A | 9/1996 | Kraus et al. |
| 5,553,619 | A | 9/1996 | Prince |
| 5,560,317 | A | 10/1996 | Bunyan et al. |
| 5,566,092 | A | 10/1996 | Wang et al. |
| 5,569,181 | A | 10/1996 | Heilman et al. |
| 5,569,208 | A | 10/1996 | Woelpper et al. |
| 5,573,515 | A | 11/1996 | Wilson et al. |
| 5,579,767 | A | 12/1996 | Prince |
| 5,583,902 | A | 12/1996 | Bae |
| 5,590,654 | A | 1/1997 | Prince |
| 5,592,940 | A | 1/1997 | Kampfe et al. |
| 5,601,086 | A | 2/1997 | Pretlow, III et al. |
| 5,611,344 | A | 3/1997 | Bernstein et al. |
| 5,616,124 | A | 4/1997 | Hague et al. |
| 5,681,285 | A | 10/1997 | Ford et al. |
| 5,687,208 | A | 11/1997 | Bae et al. |
| 5,687,708 | A | 11/1997 | Farnsworth et al. |
| 5,713,358 | A | 2/1998 | Mistretta et al. |
| 5,724,976 | A | 3/1998 | Mine et al. |
| 5,725,500 | A | 3/1998 | Micheler |
| 5,739,508 | A | 4/1998 | Uber, III |
| 5,743,266 | A | 4/1998 | Levene et al. |
| 5,768,405 | A | 6/1998 | Makram-Ebeid |
| 5,796,862 | A | 8/1998 | Pawlicki et al. |
| 5,799,649 | A | 9/1998 | Prince |

(56) References Cited

U.S. PATENT DOCUMENTS

| | | |
|---|---|---|
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,132,396 A | 10/2000 | Antanavich et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley, III et al. |
| 7,427,281 B2 | 9/2008 | Uber et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,666,169 B2 | 2/2010 | Cowan et al. |
| 7,688,057 B2 | 3/2010 | Foss et al. |
| 7,766,883 B2 | 8/2010 | Reilly et al. |
| 7,861,893 B2 | 1/2011 | Voegele et al. |
| 7,925,330 B2 | 4/2011 | Kalafut et al. |
| 8,007,487 B2 | 8/2011 | Patrick et al. |
| 8,147,464 B2 | 4/2012 | Spohn et al. |
| 8,162,903 B2 | 4/2012 | Reilly et al. |
| 8,295,914 B2 | 10/2012 | Kalafut et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,540,698 B2 | 9/2013 | Spohn et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,314,749 B2 | 4/2016 | Yagi et al. |
| 9,333,293 B2 | 5/2016 | Williams, Jr. et al. |
| 9,474,857 B2* | 10/2016 | Riley .................... A61M 5/007 |
| 9,480,788 B2 | 11/2016 | Wagner |
| 9,480,791 B2* | 11/2016 | Reilly ................. A61M 5/1422 |
| 9,555,379 B2 | 1/2017 | Schriver et al. |
| 9,855,387 B2* | 1/2018 | Small .................. A61M 5/2066 |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,391,234 B2 | 8/2019 | Sams et al. |
| 10,549,084 B2 | 2/2020 | Sokolov et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0254533 A1 | 12/2004 | Schriver et al. |
| 2005/0107697 A1 | 5/2005 | Berke et al. |
| 2005/0113754 A1 | 5/2005 | Cowan |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |

(56) References Cited

U.S. PATENT DOCUMENTS

| | | |
|---|---|---|
| 2006/0167415 A1 | 7/2006 | Nemoto |
| 2007/0068964 A1 | 3/2007 | Tanaami et al. |
| 2007/0129705 A1 | 6/2007 | Trombley, III et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1* | 1/2008 | Dlugos ............ A61M 5/486 600/37 |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0130809 A1 | 5/2010 | Morello |
| 2010/0222768 A1 | 9/2010 | Spohn et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123257 A1* | 5/2012 | Stokes, Jr. ......... A61M 5/1782 600/432 |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1 | 1/2013 | Nemoto |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2014/0027009 A1 | 1/2014 | Riley et al. |
| 2014/0142537 A1* | 5/2014 | Gibson ............ A61M 5/16831 604/67 |
| 2014/0276550 A1 | 9/2014 | Uram et al. |
| 2016/0030662 A1 | 2/2016 | Uber, III et al. |
| 2016/0278725 A1 | 9/2016 | Van Nijnatten |
| 2016/0331896 A1 | 11/2016 | Nemoto et al. |
| 2016/0331951 A1 | 11/2016 | Sokolov et al. |
| 2017/0035974 A1 | 2/2017 | Berry et al. |
| 2017/0143898 A1 | 5/2017 | Grosse-Wentrup et al. |
| 2017/0258982 A1 | 9/2017 | Kemper |
| 2017/0290971 A1 | 10/2017 | Hedmann et al. |
| 2017/0312430 A1* | 11/2017 | Schleicher ............ A61M 5/172 |
| 2017/0343446 A1 | 11/2017 | Ciolkosz et al. |
| 2018/0133392 A1 | 5/2018 | Dembo et al. |
| 2019/0083699 A1 | 3/2019 | Spohn et al. |
| 2020/0129702 A1* | 4/2020 | Pedersen ............ A61M 5/20 |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 2990073 A1 | 3/2016 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5490840 B2 | 5/2014 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |

(56) References Cited

FOREIGN PATENT DOCUMENTS

| WO | 2009051995 A1 | 4/2009 |
|---|---|---|
| WO | 2010027636 A1 | 3/2010 |
| WO | 2010117841 A1 | 10/2010 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014144651 A2 | 9/2014 |
| WO | 2014179326 A1 | 11/2014 |
| WO | 2014190264 A1 | 11/2014 |
| WO | 2015106107 A1 | 7/2015 |
| WO | 2015164783 A1 | 10/2015 |
| WO | 2016112163 A1 | 7/2016 |
| WO | 2016172467 A1 | 10/2016 |
| WO | 2016191485 A1 | 12/2016 |
| WO | 2017012781 A1 | 1/2017 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075386 A1 | 4/2018 |
| WO | 2018089882 A1 | 5/2018 |

OTHER PUBLICATIONS

"Angiography," Catheterization and Cardiovascular Diagnosis, vol. 19, pp. 123-128, 1990.

Awai Kazuo; et al, "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al., "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium vol. achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ Chem Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector—Row CT of The Thorax," pp. 47-59 (Jan. 22, 2004).

Fleischmann, D., "Present and Future Trends in Multiple Detector-Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous translumimal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of A Remotely Controlled Mechanical Pump for Injection of Contrast Medium," Catheterization and Cardiovascular Diagnosis, vol. 25, Issue 2, pp. 107-109 (Feb. 1992).

Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

Hansen, P.C., "The truncated SVD as a method for regularization," BIT Numerical Mathematics, vol. 27, Issue 4, pp. 534-555, 1987.

Harris P., H. D. "The Human Pulmonary Circulation," Edinburgh, Churchill Livingstone, (Appendix I), 1986.

Hayes, M., "Statistical Digital Signal Processing and Modeling", New York, New York, Wiley and Sons, 1996, pp. 154-177, (Prony's method).

Heiken; J.P. et al., "Dynamic Contrast-Enhanced CT of the Liver: Comparison of Contrast Medium Injection Rates and Uniphasicand Biphasic Injection Protocols", Radiology, May 1993, vol. 187, No. 2, pp. 327-331.

"Infus O.R. Multi-Drug Syringe Pump with Smart Labels," Bard MedSystems Division Inc., pp. 2693-2696 (2005).

"International Preliminary Report on Patentability from PCT Application No. PCT/US2018/048282", dated Mar. 12, 2020.

(56) References Cited

OTHER PUBLICATIONS

"International Search Report and Written Opinion from PCT Application No. PCT/US2018/048313", dated Nov. 30, 2018.
Ireland, M.A., et al., "Safety and Convenience of a Mechanical Injector Pump for Coronary Angiography,"Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System-Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential For Ultrasound Imaging of Liver," Ultrasound in Medicine & Biology, vol. 13, Issue 9, pp. 555-566 (Sep. 1987).
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, A GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
"The Solution for Your IV Formulas", Valley Lab. Inc., E-39-15, 3399, 3400, 2646.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Swiss; Medical Care., "CT Expres Contrast Media Delivery System Operation Manual Rev 1", 2004.

* cited by examiner

Fluidless Calibration Surface Plot

Rank 37  Eqn 301  $z = a+bx+cy+dx^2+ey^2+fxy$ $r^2 = 0.99854721$  DF Adj $r^2 = 0.99854638$  FitStdErr = 41.862961  Fstat = 1433086.6
a= -195.81852  b = -64.538714  c = -7438.221
d = -0.12294535  e = -1366.2935  f = -24.744878

INJECTOR PRESSURE CALIBRATION SYSTEM AND METHOD

CROSS REFERENCE TO RELATED APPLICATIONS

This application is a § U.S. national phase application under 35 U.S.C. § 371 of PCT International Application No. PCT/US2018/048313, filed 28 Aug. 2018 and claims priority to U.S. Provisional Application No. 62/552,428, titled "Fluidless Injector Pressure Calibration System and Method", filed on 31 Aug. 2017, the disclosures of which are incorporated herein in their entirety.

BACKGROUND OF THE DISCLOSURE

Field of the Disclosure

The present disclosure relates generally to systems and methods for calibrating a fluid injector, such as a medical fluid injector, and, further, to a system and method for pressure calibration of the fluid injector.

Description of Related Art

In many medical diagnostic and therapeutic procedures, a medical practitioner, such as a physician, injects a patient with one or more medical fluids. In recent years, a number of fluid delivery systems having injector-actuated syringes and fluid injectors for pressurized injection of fluids, such as a contrast solution (often referred to simply as "contrast"), a flushing agent, such as saline, and other medical fluids have been developed for use in procedures such as angiography (CV), computed tomography (CT), ultrasound, magnetic resonance imaging (MRI), positron emission tomography (PET), and other imaging procedures. In general, these fluid delivery systems are designed to deliver preset amounts of a contrast fluid, a saline flushing agent, and mixtures thereof at desired flow rates over a predetermined time.

An actual flow rate (or delivered volume) of fluid that is delivered to the patient is targeted to be as close as possible to the desired flow rate (or desired volume). However, the actual performance of the fluid delivery system is a function of many factors due to overall impedance and capacitance of the fluid delivery system. In certain delivery procedures, impedance and capacitance of the fluid delivery system may cause a fluid flow over-rate or under-rate (or volume over- or under-delivery) from a desired flow rate (or desired volume).

While various approaches exist for characterizing the performance of a fluid delivery system and correlating the desired performance with actual performance in terms of fluid flow rate and volume delivered, these approaches do not address the differences between desired and actual performance due to impedance and/or capacitance of the fluid delivery system in a comprehensive manner. As a result, existing approaches fail to address the under-delivery or over-delivery of fluid resulting from system impedance and/or capacitance. As a result, less than optimal injection boluses or discrepancies in actual fluid volume delivered may result and/or operation of the fluid delivery system can result in relatively large amounts of wasted fluid.

Accordingly, there is a need in the art for improved pressure characterization of a piston of a fluid injector. There is a further need for improved systems and methods for calibrating a fluid injector, as well as systems and methods for characterizing the performance of a fluid delivery system and correlating the desired performance with actual performance in terms of fluid flow rate and volume delivered.

SUMMARY OF DISCLOSURE

In some examples of the present disclosure, a calibration system for calibrating a pressure output of a drive member of a fluid injector. In specific embodiments, the calibration system may be a fluidless calibration system, which may be readily utilized between several different fluid injection systems on site and/or by an imaging technician without the presence of a trained service technician. The calibration system may store data on drive members of a fluid injector over a period of time and determine if, how, and when the drive member falls out of specification. The calibration system may be utilized for each drive member of a fluid injector, such as a fluid injector with one, two, three, or even more drive members. The calibration system may be suited to calibrate the motor force of a fluid injector having one or more pistons as drive members, such as a syringe based fluid injector system, for example a fluid injector having one, two, three, or more pistons for operatively engaging corresponding plungers or piston engagement members of one, two, three, or more syringes.

According to an embodiment, the calibration system may comprise a housing configured for connecting to the fluid injector; a drive member engagement portion configured for contacting a drive member of the fluid injector; a compressible member connected at its proximal end to the drive member engagement portion; and a sensor connected to the compressible member. The compressible member may be compressed with movement of the drive member of the fluid injector between a first, uncompressed position and a second, at least partially compressed position of the fluid injector in a distal direction. The sensor may be configured for measuring a force imparted by the drive member when the compressible member is in the second, at least partially compressed position compared to when the drive member is in the first, uncompressed position. The sensor may be a strain gauge, a force sensor, a load cell, a pressure sensor, a force transducer, and combination of any thereof. In specific embodiments, the sensor is a strain gauge and in other embodiments the sensor is a force sensor. According to various embodiments, the compressible member may be a spring, a plurality of springs, a pneumatic compression cell, a hydraulic compression cell, a compressible foam, an elastomer, and combinations of any thereof. In specific embodiments the compressible member is a spring. According to certain embodiments, the sensor may be in wired or wireless communication with a processor of the fluid injector and an output of the sensor may be transmitted to the processor. In certain aspects, the output of the sensor may be used to calibrate an input to one or more of a motor, the drive member, a ball screw in mechanical communication with the motor and the drive member, a frictional component from a disposable fluid delivery reservoir, and other compressible mechanical components. In various aspects, the output of the sensor may be used to generate a calibration curve for calibrating a pressure output of the drive member of the fluid injector. In specific aspects, the calibration curve is utilized to determine a fault condition, such as, for example, a warning that the drive member or motor may need servicing.

According to various embodiments, the present disclosure describes a calibration system for calibrating a pressure output of a drive member of fluid injector where the calibration system comprises: a housing configured for connecting to the fluid injector; a drive member engagement portion configured for contacting a drive member of the fluid injector; a compressible member having a known modulus of compression connected at its proximal end to the drive member engagement portion; and a sensor connected to the compressible member. The compressible member may be compressed with movement of the drive member of the fluid injector between a first, uncompressed position and a second, at least partially compressed position of the fluid injector in a distal direction. The sensor may be configured for measuring a displacement of the drive member when the compressible member is in the second, at least partially compressed position compared to when the drive member is in the first, uncompressed position. The compressible member may be selected from a spring, a plurality of springs, a pneumatic compression cell, a hydraulic compression cell, a compressible foam, an elastomer, or combinations of any thereof. According to specific embodiments, the compressible member is a spring. According to various embodiments, the sensor may be in wired or wireless communication with a processor of the fluid injector and an output of the sensor may be transmitted to the processor. The processor may determine the pressure output of the drive member of the fluid injector from the output of the sensor and the modulus of compression of the compressible member. In various embodiments, the output of the sensor may be used to generate a calibration curve for calibrating the pressure output of a drive member of the fluid injector. In specific aspects, the calibration curve is utilized to determine a fault condition, such as, for example, a warning that the drive member or motor may need servicing.

In certain embodiments, the calibration system can be regularly used to track changes in load for the drive member over time. The calibration system may be utilized daily, weekly, monthly, or at other regular or irregular intervals to track changes in the calibration of the injector. In certain embodiments, the calibrations may be done by the imaging technician without need for service calls from the injector manufacturer representatives or third party servicing technicians. In other embodiments, the calibrations may be recorded over a period of time and may be used by a servicing technician to determine whether specific services may be required. Changes in calibration of the injector that fall outside of expected values and tolerances may signify potential unexpected wear or defects with the injector system and allow early detection and servicing.

In other examples of the present disclosure, a method of calibrating a pressure output of a drive member of a fluid injector. According to various embodiments, the method may comprise: connecting a calibration system to the fluid injector; contacting a drive member of the fluid injector with the drive member engagement portion of the calibration system; driving a motor of the fluid injector to move the drive member and compress the compressible member from a first, uncompressed positon to a second, at least partially compressed position; and generating a measurement signal by a sensor based on the a force imparted on the compressible member by the drive member or the displacement of the drive member when the compressible member is in the second, at least partially compressed position. The methods may be used by any of the various embodiments of the calibration systems described herein. In certain embodiments, the method may further include sending the measurement signal to a processor of the fluid injector to calibrate a pressure output of the drive member based on the measurement signal. In still further embodiments, the methods may include generating a calibration curve for the pressure output of the drive member. The method may further include comparing a calibration measurement signal with one or more previous measurement signals and/or with a predetermined calibration value to determine if the injector calibration falls outside of tolerances.

Various aspects of the system and method for pressure calibration of the fluid injector are disclosed in one or more of the following numbered clauses:

Clause 1. A calibration system for calibrating a pressure output of a drive member of a fluid injector, the calibration system comprising: a housing configured for connecting to the fluid injector; a drive member engagement portion configured for contacting a drive member of the fluid injector; a compressible member connected at its proximal end to the drive member engagement portion, wherein the compressible member is compressed with movement of the drive member of the fluid injector between a first, uncompressed position and a second, at least partially compressed position of the fluid injector in a distal direction; and a sensor connected to the compressible member, wherein the sensor is configured for measuring a force imparted by the drive member when the compressible member is in the second, at least partially compressed position.

The various embodiments of the calibration system provide useful data related to force applied by a drive member in a single stroke across an entire expected load regime. Conventional fluid calibration has a fixed orifice which reaches a set pressure when the drive member is moved at a standard speed. This requires collection of multiple different pressure points to generate a calibration profile for several drive speeds. In the various embodiments of the methods described herein, the sensor determines all loads at a given speed in a single stroke of the drive member. As the compressible member is compressed, the system travels through the entire expected load regime in a single stroke.

Clause 2. The calibration system of clause 1, wherein the sensor is selected from the group consisting of a strain gauge, a force sensor, a load cell, a pressure sensor, a force transducer, and combination of any thereof.

Clause 3. The calibration system of clause 2, wherein the sensor comprises a strain gauge.

Clause 4. The calibration system of clause 2, wherein the sensor comprises a force sensor.

Clause 5. The calibration system of any of clauses 1 to 4, wherein the compressible member is selected from the group consisting of a spring, a plurality of springs, a pneumatic compression cell, a hydraulic compression cell, a compressible foam, an elastomer, and combinations of any thereof.

Clause 6. The calibration system of clause 5, wherein the compressible member is a spring.

Clause 7. The calibration system of any of clauses 1 to 6, wherein the sensor is in wired or wireless communication with a processor and an output of the sensor is transmitted to the processor.

Clause 8. The calibration system of any of clauses 1 to 7, wherein an output of the sensor is used to calibrate an input to one or more of a motor, the drive member, a ball screw in mechanical communication with the motor and the drive member, a frictional component from a disposable fluid delivery reservoir, and other compressible mechanical components.

Clause 9. The calibration system of any of clauses 1 to 8, wherein an output of the sensor is used to generate a calibration curve for calibrating a pressure output of the drive member of the fluid injector.

Clause 10. The calibration system of clause 9, wherein the calibration curve is utilized to determine or predict a fault condition.

Clause 11. A calibration system for calibrating a pressure output of a drive member of fluid injector, the calibration system comprising: a housing configured for connecting to the fluid injector; a drive member engagement portion configured for contacting a drive member of the fluid injector; a compressible member having a known modulus of compression connected at its proximal end to the drive member engagement portion, wherein the compressible member is compressed with movement of the drive member of the fluid injector between a first, uncompressed position and a second, at least partially compressed position of the fluid injector in a distal direction; and a sensor connected to the compressible member, wherein the sensor is configured for measuring a displacement of the drive member when the compressible member is in the second, at least partially compressed position.

Clause 12. The calibration system of clause 11, wherein the compressible member is selected from the group consisting of a spring, a plurality of springs, a pneumatic compression cell, a hydraulic compression cell, a compressible foam, an elastomer, and combinations of any thereof.

Clause 13. The calibration system of clause 12, wherein the compressible member is a spring.

Clause 14. The calibration system of any of clauses 11 to 13, wherein the sensor is in wired or wireless communication with a processor and an output of the sensor is transmitted to the processor.

Clause 15. The calibration system of clause 14, wherein the processor determines the pressure output of the fluid injector from the output of the sensor and the modulus of compression of the compressible member.

Clause 16. The calibration system of any of clauses 11 to 15, wherein an output of the sensor is used to generate a calibration curve for calibrating the pressure output of a drive member of the fluid injector.

Clause 17. The calibration system of clause 16, wherein the calibration curve is utilized to determine a fault condition.

Clause 18. A method of calibrating a pressure output of a drive member of a fluid injector, the method comprising: connecting a calibration system to the fluid injector, the calibration system comprising: a housing configured for connecting to the fluid injector; a drive member engagement portion configured for contacting a drive member of the fluid injector; a compressible member having a known modulus of compression connected at its proximal end to the drive member engagement portion, wherein the compressible member is compressed with movement of the drive member of the fluid injector between a first, uncompressed position and a second, at least partially compressed position of the fluid injector in a distal direction; and a sensor connected to the compressible member, wherein the sensor is configured for measuring one of a force imparted by the drive member and a displacement of the drive member when the compressible member is in the second, at least partially compressed position; contacting a drive member of the fluid injector with the drive member engagement portion of the calibration system; driving a motor of the fluid injector to move the drive member and compress the compressible member from the first, uncompressed positon to the second, at least partially compressed position; and generating a measurement signal by the sensor based on the a force imparted on the compressible member by the drive member or the displacement of the drive member when the compressible member is in the second, at least partially compressed position.

Clause 19. The method of clause 18, further comprising sending the measurement signal to a processor to calibrate a pressure output of the drive member based on the measurement signal.

Clause 20. The method of clause 18 or 19, further comprising generating a calibration curve for the pressure output of the drive member.

These and other features and characteristics of a system for pressure calibration of the fluid injector, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
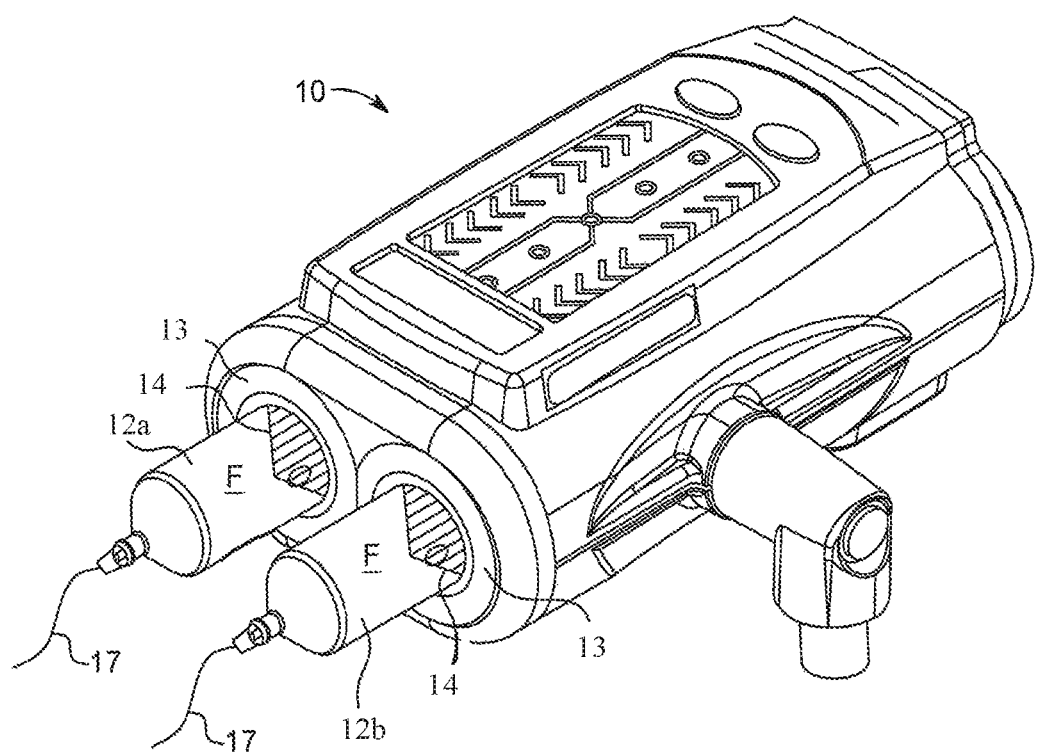
FIG. 1 is a perspective view of a fluid delivery system according to an example of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to fluid injector and a system and method for a pressure calibration of the fluid injector. Associated disclosure related to capacitance development and issues associated with fluid injection system is described in PCT International Application No. PCT/US2017/020637, filed 3 Mar. 2017, the disclosure of which is incorporated herein by this reference.

Characterizing an impedance of a fluid delivery system to minimize a difference between desired and actual fluid delivery system performance requires consideration of how energy from an energy source, such as a pressurizing mechanism, for example a drive member such as a piston attached to a motor, is used in or moves through the system. The energy output or loss from the fluid delivery system may be in the form of heat losses through frictional forces or of work done on the fluid delivery system. For example, some of the energy carried by the pressurized fluid as it is delivered under pressure through a catheter is lost through resistive, frictional, or dissipative heating of the fluid. Additionally, pressurized delivery of fluid can also increase the potential energy of the system in terms of an increase in overall volume of system components and/or compressive forces on system components, as discussed herein. For example, under the pressurized fluid force, system components may expand or may compress under the stress or load imparted by the pressurized fluid in a closed or open system. Furthermore, the kinetic energy of pressurized fluid moving through the fluid delivery system can affect the overall performance of the fluid delivery system. For example, inertial forces of moving contrast media, saline, compression of system mechanical components, and expansion of the reservoirs, syringes, and/or tubing associated with the system may cause a phase lag between movement of the syringe plunger within the injector syringe and movement of contrast material out of the catheter and into the patient.

Due to high injection pressures, which can range from 100 psi up to on the order of 1,200 psi in some angiographic procedures, there may be an expansion, deflection, or compression of various components of the fluid delivery system, such as expansion of the fluid reservoirs, such as syringes and tubing, and compression of mechanical components, such as gearing and drive components of the fluid injector that apply the pressure, such that there may be an increased volume of fluid in the syringe and tubing in excess of the desired quantity selected to be delivered in the injection procedure. Such increase in the volume of fluid in the fluid reservoir or tubing occurs due to increased system capacitance (i.e., increased fluid volume capacity). Total system capacitance (also referred to as compliance or elasticity) represents the volume of fluid (i.e., change in volume, such as excess volume) that is captured in the swelling of components of the fluid delivery system and compression of mechanical components. In general, capacitance is directly correlative to injection pressure and directly correlative to volume of contrast medium and saline in the syringes. In other words, capacitance increases with an increase in injection pressure and an increase in volume of fluid in the syringes. Total system capacitance is inherent to each fluid delivery system and depends on a plurality of factors beyond pressure and volume of fluid remaining in the system, including, without limitation, fluid properties (such as viscosity, temperature, etc.), injector construction, mechanical properties of materials used to construct the syringe or reservoir, plunger, pressure jacket surrounding the syringe, fluid lines delivering the fluid to the patient, size of the syringe, plunger, pressure jacket, diameter of tubing or other orifices through which the fluid must pass under pressure, and fluid properties, such as temperature, viscosity, and density. System capacitance may result in discrepancies between programed fluid volume delivery and actual volume delivery. For example, when beginning a pressurized fluid delivery, initial pressurization may result in swelling of system components under fluid pressure and/or compression of mechanical components under force, rather than delivery of a corresponding fluid volume to a patient. When the pressurizing force is reduced or released during a portion of the injection, for example when the desired fluid volume is delivered, the release of the stored capacitance-based volume may result in over delivery of fluid.

In some fluid delivery systems, such as fluid delivery systems having a single syringe, two syringes (for example a contrast media syringe and a saline flush syringe), three syringes (for example two contrast syringes, which may contain the same or different contrast media or different concentrations, and a saline flush syringe) or a plurality of syringes, each independently driven by pistons or drive members of the fluid injector, the accuracy of fluid delivery is based, at least in part, on the ability of the fluid injector to accurately characterize the pressure in the syringe(s) and fluid path(s). This characterization may be based, at least in part, on calibrating the piston/drive member using a calibration station configured for accurately measuring the pressure imparted on a fluid by the piston/drive member. Pressure calibration of fluid injectors may be performed by pushing fluid at varying rates through a frictionless fixture with a fixed orifice. Pressure of the fluid may then be measured using a pressure gauge, where a real pressure signal is either recorded or fed back into the fluid injector to correlate the load signal of the piston, such as voltage or current measurement, to a real pressure value. Conventional calibration stations which involve pressurization of fluid filled syringes and measurement of resulting fluid pressures can be cumbersome, difficult to set up and operate, and have compounded errors, leading to inaccurate pressure characterization of the piston or drive member. For example, errors which may affect calibration measurements may include friction in the fixture, air in the fluid path, lack of data points on a correlative timescale, fluid leakage inaccuracies, and gauge reading inaccuracies. Further, conventional calibration does not readily provide for real-time adjustment based on factors, such as component wear, differences in syringe tolerance, fluid characteristics, and volumes of syringes used since it is typically performed infrequently, such as when the injector is serviced. Changes in tolerances and system wear in injector components can add up over time to increase volume inaccuracies, creating error in previous calibrations of the volume accuracies of fluid delivery. According to various embodiments herein, a calibration system is described which can quickly and accurately measure and calibrate pressurization forces in a fluid injector system, such as for drive members or pistons. The calibration system may be readily used by a imaging technician, for example on a daily, weekly, and/or monthly basis to measure and monitor the calibration of a fluid injector system over time and further, may allow for calibration corrections for more accurate fluid delivery. In other embodiments, the calibration system may work with a processor to track system characteristics over time, providing information about component status over time to determine whether system components are operating within specification or are in need of servicing or replacement.

According to an embodiment, the calibration system may comprise a housing configured for connecting to and/or engaging with the fluid injector; a drive member engagement portion configured for contacting an a drive member of the fluid injector; a compressible member connected at its proximal end to the drive member engagement portion; and a sensor connected to the compressible member. The compressible member may be compressed with movement of the drive member of the fluid injector between a first, uncompressed position and a second, at least partially compressed position of the fluid injector in a distal direction. The sensor may be configured for measuring a force imparted by the drive member when the compressible member is in the second, at least partially compressed position compared to when the drive member is in the first, uncompressed position. The sensor may be a strain gauge, a force sensor, a load cell, a pressure sensor, a force transducer, and combination of any thereof. Alternatively, if the modulus of the compressible member is known, the force applied may be calculated utilizing an algorithm, such as Hooke's Law. In specific embodiments, the sensor is a strain gauge and in other embodiments the sensor is a force sensor. According to various embodiments, the compressible member may be a spring, a plurality of springs, a pneumatic compression cell, a hydraulic compression cell, a compressible foam, an elastomer, an opposing ferro- or electromagnetic repulsive force (which may be varied) to provide resistance to drive member movement, a deflectable metal member, and combinations of any thereof. In specific embodiments the compressible member is a spring. According to certain embodiments, the sensor may be in wired or wireless (e.g., by WiFi network, Bluetooth, Ethernet, or other conventional wireless communication technology) communication with one or more of a processor of the fluid injector, an external processor, and a hospital information network, and an output of the sensor may be transmitted to the one or more of a processor of the fluid injector, an external processor, and a hospital information network. In certain aspects, the output of the sensor may be used to calibrate an input to one or more of a motor, the drive member, a ball screw in mechanical communication with the motor and the drive member, a frictional component from a disposable fluid delivery reservoir, and other compressible mechanical components. In various aspects, the output of the sensor may be used to generate a calibration curve for calibrating a pressure output of the drive member of the fluid injector. In specific aspects, the calibration curve is utilized to determine a fault condition, such as, for example, a warning that the drive member or motor may need servicing. For example, by frequent calibration using a injector calibration system as described according to the various embodiments herein, a processor may notice gradual or sudden deviations in the pressure calibration which may be the result of degradation of or out-of-specification readings for one or more system components According to various embodiments, the present disclosure describes a calibration system for calibrating a pressure output of a drive member of fluid injector where the calibration system comprises: a housing configured for connecting to the fluid injector; a drive member engagement portion configured for contacting a drive member of the fluid injector; a compressible member having a known modulus of compression connected at its proximal end to the drive member engagement portion; and a sensor connected to the compressible member. The compressible member may be compressed with movement of the drive member of the fluid injector between a first, uncompressed position and a second, at least partially compressed position of the fluid injector in a distal direction. The sensor may be configured for measuring a displacement of the drive member when the compressible member is in the second, at least partially compressed position compared to when the drive member is in the first, uncompressed position. The compressible member may be selected from a spring, a plurality of springs, a pneumatic compression cell, a hydraulic compression cell, a compressible foam, an elastomer, or combinations of any thereof. According to specific embodiments, the compressible member is a spring. According to various embodiments, the sensor may be in wired or wireless communication with a processor of the fluid injector and an output of the sensor may be transmitted to the processor. The processor may determine the pressure output of the drive member of the fluid injector from the output of the sensor and the modulus of compression of the compressible member. For example, when the modulus of compression of the compressible member and the distance between the first, uncompressed state and the second, at least partially compressed state are known, the force that must be applied to the compressible member to compress from the first state to the second state may be calculated. In certain embodiments, wherein the compressible member is a spring having a known spring constant, the force that must be applied to the spring to compress the spring may be calculated using Hooke's Law ($F_s = -k \cdot x$, where $F_s$ is the force applied, k is the spring constant and x is the distance compressed). According to other embodiments, where the compressible member comprises another compressible material, the modulus of compression may be initially determined by applying a known force of compression and measuring the distance of compression and developing an equation that shown the functional relationship between the force of compression and distance compressed. This equation may then be utilized by a processor to calculate the force of compression applied to the calibration system according to various embodiments. In various embodiments, the output of the sensor may be used to generate a calibration curve for calibrating the pressure output of a drive member of the fluid injector. In specific aspects, the calibration curve is utilized to determine a fault condition, such as, for example, a warning that the drive member or motor may need servicing.

In certain embodiments, the calibration system can be regularly used to track changes in load for the drive member over time. The calibration system may be utilized daily, weekly, monthly, or at other regular or irregular intervals to track changes in the calibration of the injector. In certain embodiments, the calibrations may be done by the imaging technician without need for service calls from the injector manufacturer representatives or third party servicing technicians. In other embodiments, the calibrations may be recorded over a period of time and may be used by a servicing technician to determine whether specific services may be required. Changes in calibration of the injector that fall outside of expected values, specifications, and tolerances may signify potential unexpected defects or general wear with one or more components of the injector system and allow early detection and servicing. Injector components that may show defects or wear include but are not limited to motors, drive trains, ball drives, gearing, drive member components, syringe and/or plunger engagement or locking mechanisms, restraining members and components that restrain or engage one or more disposable or reusable components, electromechanical components, etc.

In other examples of the present disclosure, a method of calibrating a pressure output of a drive member of a fluid injector. According to various embodiments, the method may comprise: connecting a calibration system to the fluid injector; contacting a drive member of the fluid injector with the drive member engagement portion of the calibration system; driving a motor of the fluid injector to move the drive member and compress the compressible member from a first, uncompressed positon to a second, at least partially compressed position; and generating a measurement signal by a sensor based on the a force imparted on the compressible member by the drive member or the displacement of the drive member when the compressible member is in the second, at least partially compressed position. The methods may be used by any of the various embodiments of the calibration systems described herein. In certain embodiments, the method may further include sending the measurement signal to one or more of a processor of the fluid injector, an external processor, a hospital information system, and to a manufacturer or service provider to calibrate a pressure output of the drive member based on the measurement signal. In still further embodiments, the methods may include generating a calibration curve for the pressure output of the drive member. The method may further include comparing a calibration measurement signal with one or more previous measurement signals and/or with a predetermined calibration value to determine if the injector calibration falls outside of specifications or tolerances. According to certain embodiments, a calibration curve may be created as a factory setting and/or may be generated and updated continuously by the processor, so that sudden deviations from the calibration curve may indicate degradation of operation outside of specifications or tolerances, imminent failure, or failure of one or more injector components.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast media or other medical fluid and a second syringe 12b for delivering saline or other medically approved flushing agent to flush the contrast media to the patient. In other embodiments, the fluid injector 10 may have three syringes 12, a first and second syringe for delivering one or two different contrast media or other medical fluid and a third syringe for delivering saline or other medically approved flushing agent to flush the contrast media to the patient. According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast media from the tubing into the patient). According to various embodiments, the fluid injector 10 may be configured to deliver the contrast and saline separately or as a mixture (e.g., delivering a specific volume saline over a specific time followed by delivering a specific volume of contrast, delivering a specific volume contrast over a specific time followed by delivering a specific volume of saline, or a volume of contrast followed by a specified ratio of contrast and saline (i.e., in a "dual flow" process) over a specific time, followed by a second volume of saline over a specified time to flush the contrast media from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12a,b with fluid and in certain embodiments, the fluid injector 10 may have a plurality of bulk fluid source, one for each of the plurality of syringes, for filling each of the plurality of syringes with the desired fluid.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
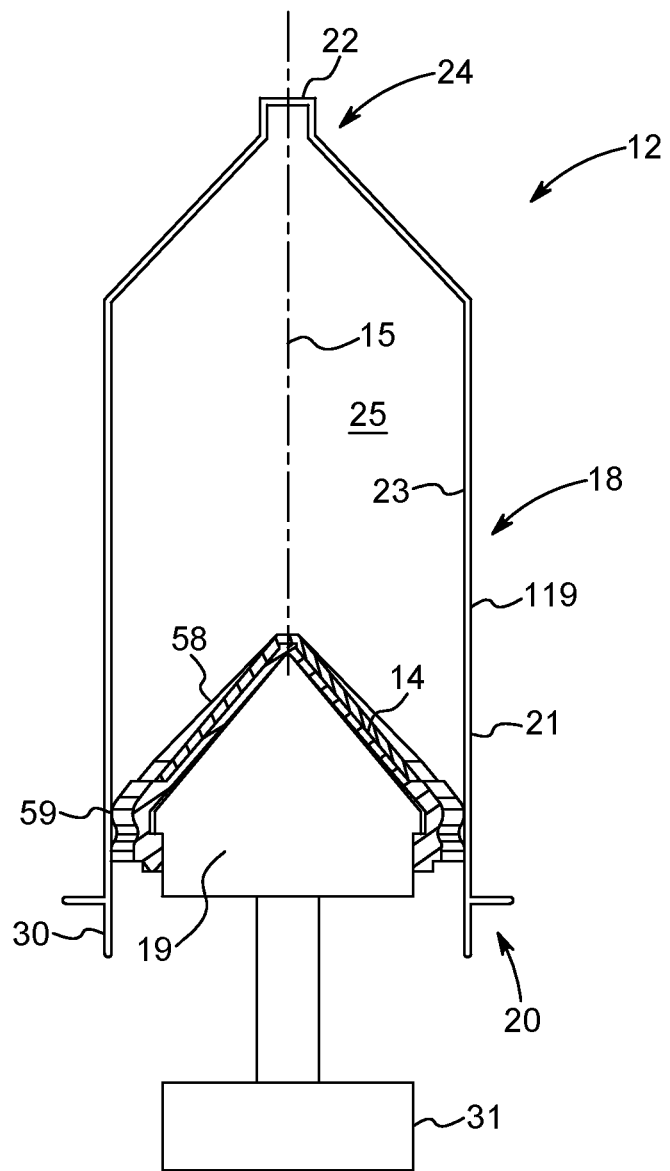
FIG. 2 is a side cross-sectional view of a syringe configured for use with the fluid delivery system of FIG. 1.

With reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication No. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced moved through the barrel 18.

With continued reference to FIG. 2, the proximal end 20 of the syringe 12 is sized and adapted for being removably inserted in a syringe port 13 of an injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

The syringe 12 may be made of any suitable medical-grade plastic or polymeric material, desirably a clear or substantially translucent plastic material. The material of the syringe 12 is desirably selected to meet the required tensile and planar stress requirements, water vapor transmission, and chemical/biological compatibility. Exemplary syringes suitable for use with the injector 10 depicted in FIG. 1 are described in U.S. Pat. Nos. 5,383,858; 6,322,535; 6,652,489; 9,173,995; and 9,199,033, the disclosures of which are all incorporated by reference in their entirety.

Figure 3:
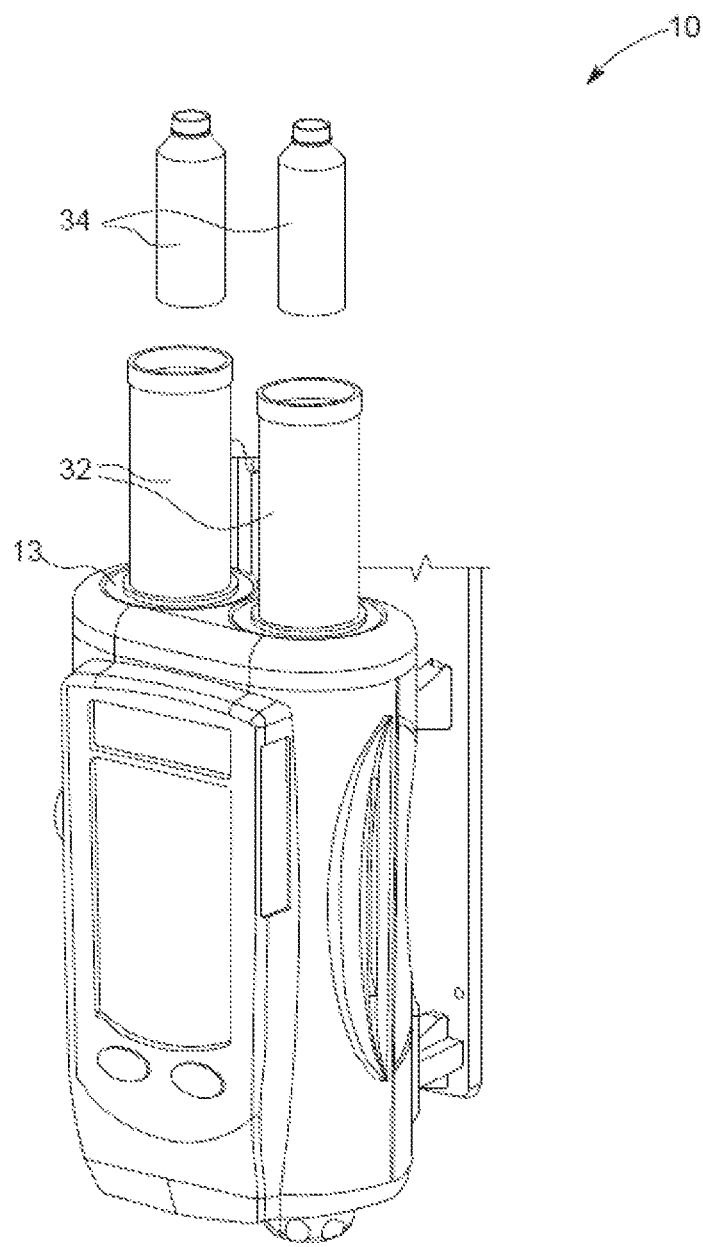
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4:
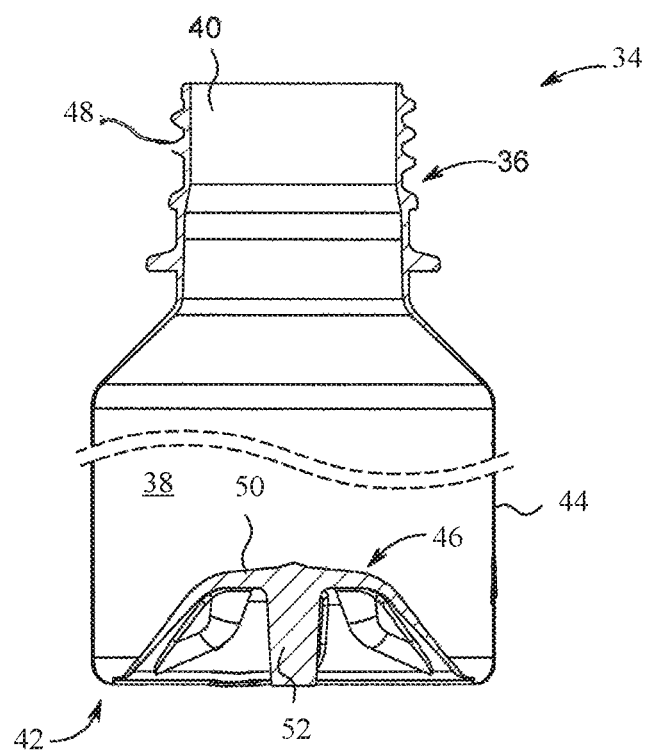
FIG. 4 is a side cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending therebetween. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
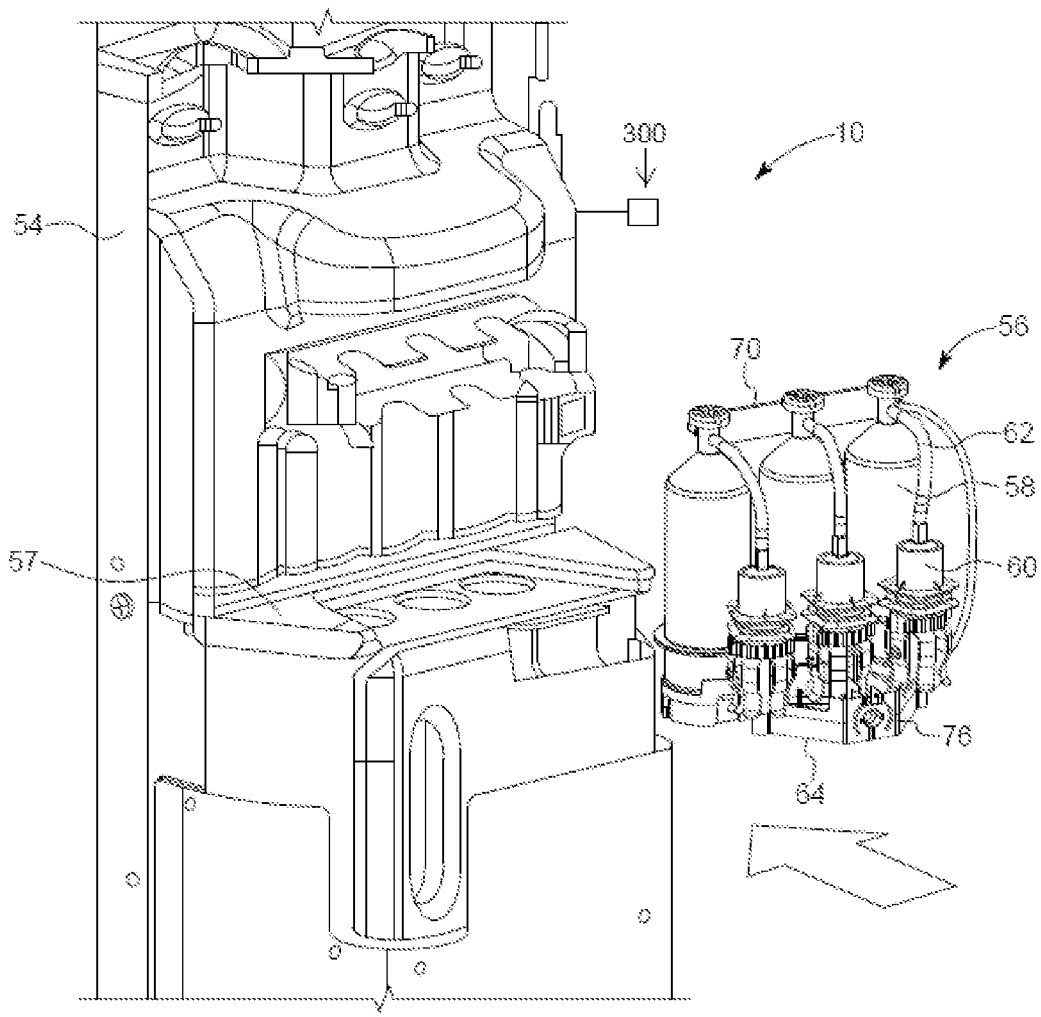
FIG. 5 is a perspective view of a fluid delivery system according to another example of the present disclosure.

With reference to FIG. 5, a fluid injector 10 is illustrated in accordance with another example of the present disclosure. The injector 10 has a housing 54 that encloses various mechanical drive components and electrical and power components necessary to drive various mechanical drive components, control components, such as electronic memory and electronic control devices used to control operation of reciprocally movable drive members (not shown). The fluid injector 10 further has a multi-use disposable system (MUDS) 56 suitable for use over multiple injection protocols that is removably connectable with the fluid injector 10. The MUDS 56 may be connected with the fluid injector 10 by a retaining mechanism 57 that engages a distal portion of the three syringes 58 of the MUDS 56, to releasably secure the MUDS 56 within the injector 10. Injector 10 and the corresponding MUDS 56 as illustrated in FIG. 5 are described in detail in WO 2016/112163, the disclosure of which is incorporated herein by this reference.

Figure 6:
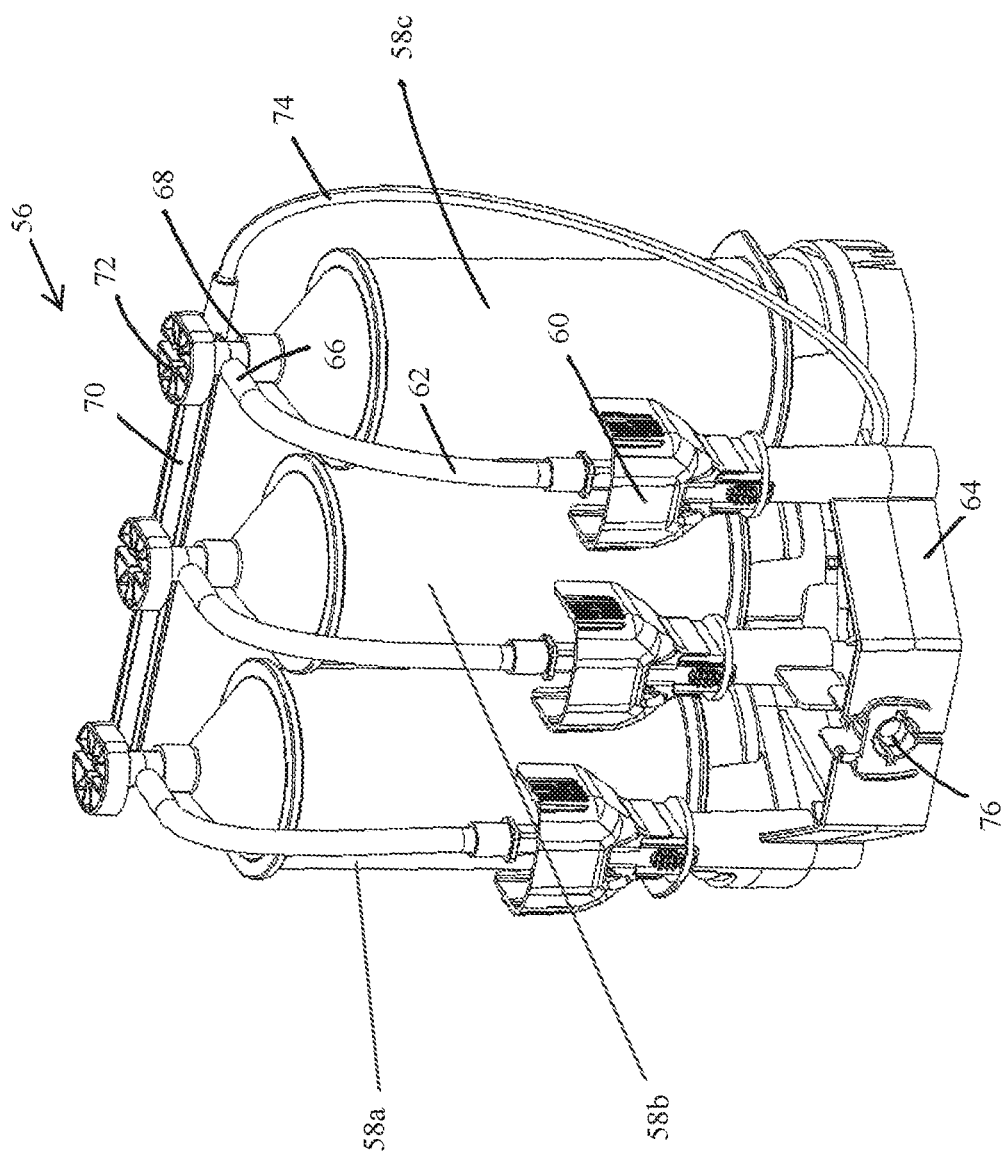
FIG. 6 is a front perspective view of a multi-use disposable system configured for use with the fluid delivery system of FIG. 5.

The MUDS 56 may comprise one or more syringes or pumps 58. In some aspects, the number of syringes 58 corresponds to the number of drive members/pistons on the fluid injector 10. In some examples, such as shown in FIGS. 5 and 6, the MUDS 56 has three syringes 58 arranged in a side-by-side arrangement. Each syringe 58 has a bulk fluid connector 60 for connecting to a respective bulk fluid source (not shown) via a MUDS fluid path 62. The MUDS fluid path 62 may be formed as a flexible tube that connects to the bulk fluid connector 60 having a spike element at its terminal end.

With reference to FIG. 6, the MUDS 56 has a frame 64 for supporting the one or more syringes 58a-58c. The syringes 58a-58c may be removably or non-removably connected to the frame 64. Each syringe 58a-58c has an elongated, substantially cylindrical syringe body. Each syringe 58a-58c has a filling port 66 in fluid communication with the MUDS fluid path 62 for filling the syringe 58a-58c with fluid from a bulk fluid source. Each syringe 58a-58c further has a discharge outlet or conduit 68 at the terminal portion of its distal end. The discharge outlet 68 of each syringe 58a-58c is in fluid communication with a manifold 70. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 70 has a fluid pathway that is in fluid communication with each syringe 58a-58c and with a fluid outlet line 74 in fluid communication with a port 76 configured for connecting to a single use fluid path element (not shown) for delivering fluid to the patient.

In various embodiments, for fluid injector 10, for example any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts, that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31.

Figure 7:
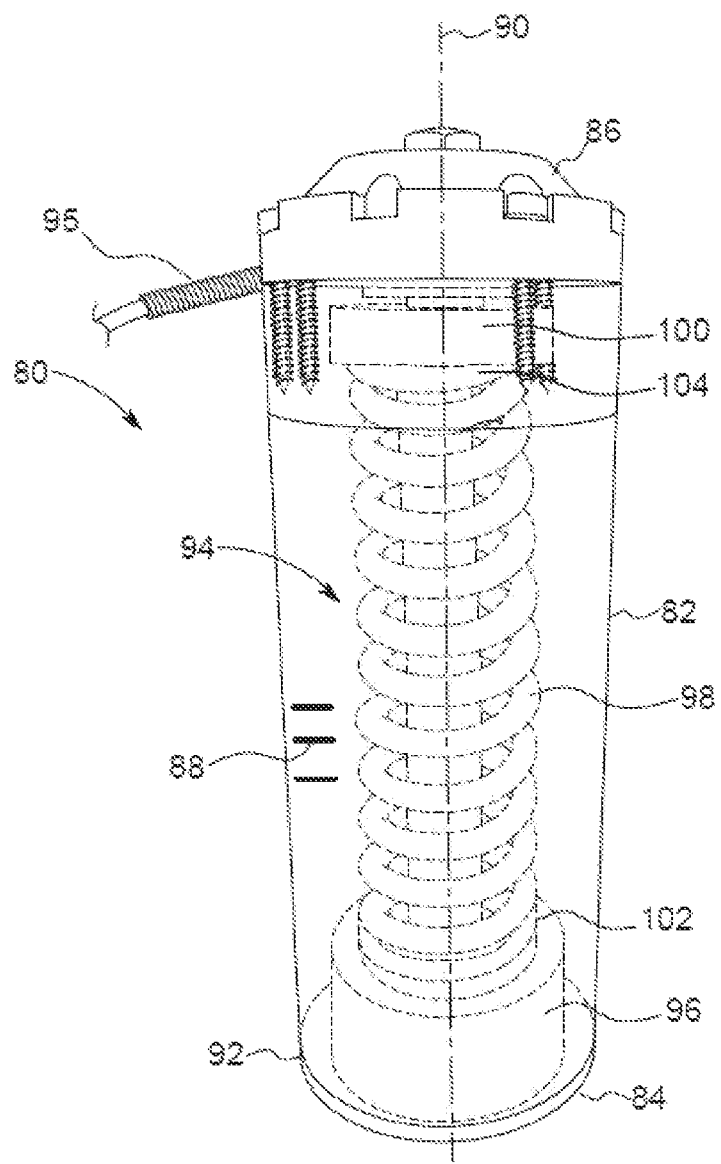
FIG. 7 is a front perspective view of a calibration fixture in accordance with an example of the present disclosure.
Figure 8:
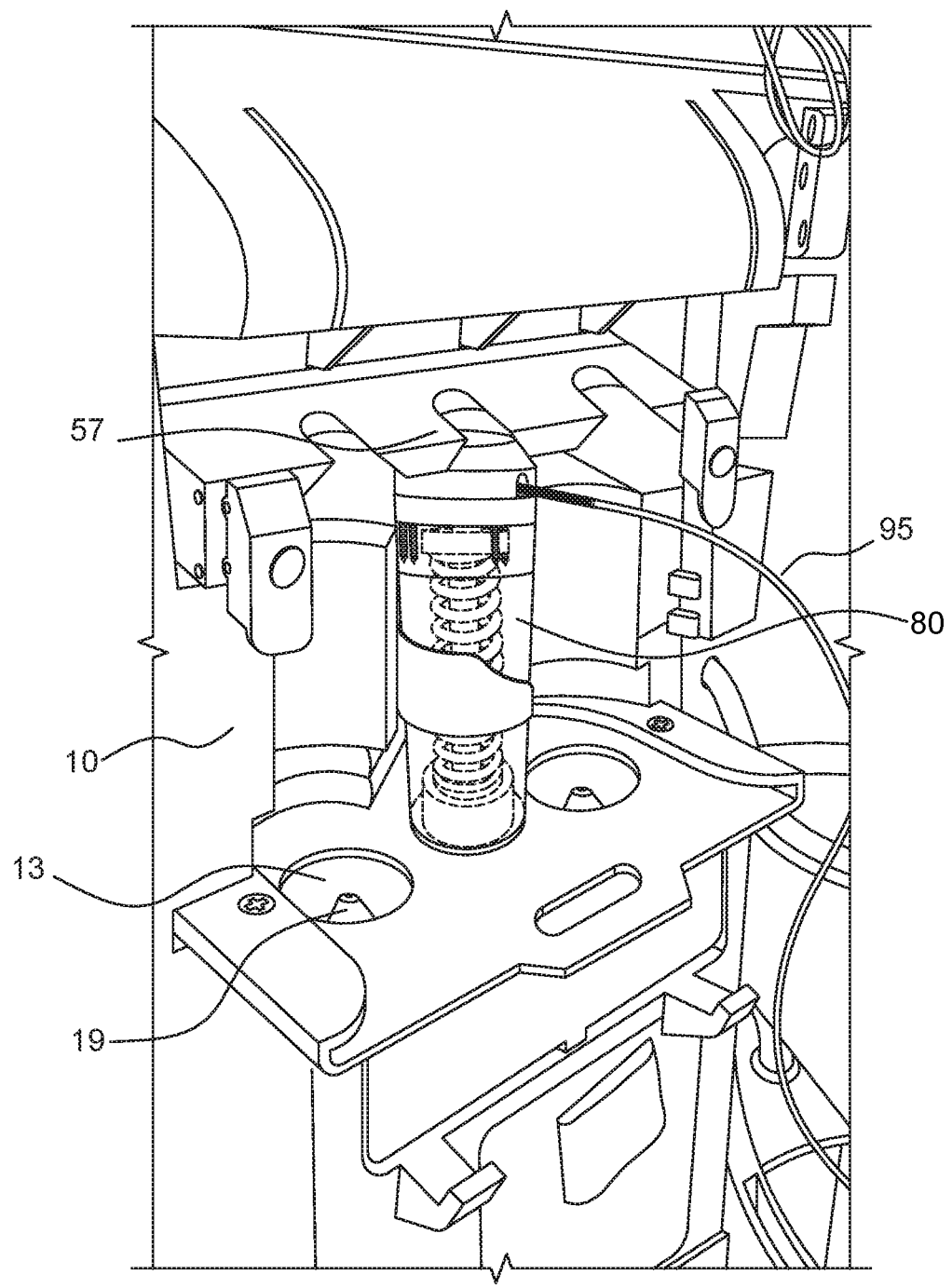
FIG. 8 is a front perspective view of the calibration fixture of FIG. 7 in use with the fluid delivery system shown in FIG. 5.

FIG. 7 illustrates one example of an embodiment of a fluidless embodiment of pressure calibration system 80 (hereinafter referred to as "calibration system 80") of the present disclosure. The calibration system 80 is configured for connecting to one or more drive members 19 of a fluid injector 10 (FIG. 8), such as any of the fluid injectors 10 shown in FIGS. 1, 3, and 5, for performing a calibration routine to calibrate the pressure output of the individual motors and drive systems of the fluid injector 10. While calibration system 80 is illustrated as being configured to engage with a single drive member of a fluid injector, calibration systems including multiple housing set-ups for engaging with two, three, or all drive members of a specific fluid injector are envisioned and within the bounds of the present disclosure. While traditional calibration systems use fluid-filled syringes having a pressure transducer at the syringe outlet, these calibration systems have inherent limitations, such as due to fluid contamination. The calibration system 80 disclosed herein avoids these limitations inherent in the prior art by eliminating the need for fluid in the calibration process while allowing for ready monitoring and calibration of a system without requiring a service technicians presence, allowing for early diagnosis of system issues, such as out of specification behavior of one or more injector components.

With continued reference to FIG. 7, the calibration system 80 has a housing 82 configured for connecting with the fluid injector 10. In some examples, the housing 82 is configured for connecting with the syringe port 13 of the fluid injector 10 (shown in FIG. 8) in a manner similar to the connection between the syringe 12 and the fluid injector 10 shown in FIGS. 1, 3, and 5. The housing 82 has a proximal end 84 and a distal end 86, with a sidewall extending therebetween along a length of a longitudinal axis 90 extending through a center of the housing 82. In some examples, the distal end 86 may have a conical shape that narrows in a distal direction, similar to the distal end of the syringe 12. When used with the fluid injector 10 shown in FIG. 5, the distal end 86 may be configured for engaging the retaining mechanism 57 (see, e.g., FIG. 8). The proximal end 84 of the housing 82 may be sized and adapted for being removably inserted in or otherwise engaged with the syringe port 13 of the injector 10 (shown in FIGS. 1, 3, 5, and 8). In some examples, the proximal end 84 of the housing 82 defines an engagement section 92 that is configured to be removably inserted into (or otherwise engaged with) the syringe port 13 of the injector 10 while the remaining portion of the housing 82 remains outside of the syringe port 13. In some examples, the housing 82 may have one or more position markers 88 which may be used by an optical system (not shown) to determine a position of the drive member/piston 19 or piston engagement portion 96, for example as the drive member/piston 19 or piston engagement portion 96 moves from a first, uncompressed positon to a second, at least partially compressed position. Alternatively, the drive system may determine the distance traveled by the drive member/piston 19 as it moves from the first, uncompressed positon to the second, at least partially compressed position, and deliver that distance information to a processor associated with the injector 10, as described herein.

With continued reference to FIG. 7, the housing 82 includes a compressible member 94 having a drive member engagement portion 96, and a sensor 100, such as a force gauge. The compressible member 94 may include a one or more compressible springs 98 or other compressible components as described herein. The drive member engagement portion 96 is configured for contacting or connecting with the drive member 19 of the fluid injector 10 (shown in FIG. 8). In certain embodiments, the drive member engagement portion 96 may connect with the drive member 19 in a manner similar to the connection between the plunger 16 and the drive member 19 described herein with reference to FIGS. 1-2. The drive member engagement portion 96 may have the same connection features as the plunger 16 to allow the compressible member 94 and sensor 100 to be connected to the drive member 19 such that the drive member engagement portion 96 and compressible member can be moved in a reciprocal manner within the housing 82 in a direction along the longitudinal axis 90. In other embodiments, the drive member 19 may abut and contact a proximal surface of the drive member engagement portion 96, such that when a distal force is applied by the drive member 19, the drive member engagement portion 96 is moved in the distal direction with concurrent compression of the compressible member 94.

With continued reference to FIG. 7, the compressible member 94, such as the one or more compressible springs 98 may have a proximal end 102 connected with the drive member engagement portion 96 and a distal end 104 connected with a sensor 100, such as a strain gauge, a force sensor, a load cell, a pressure sensor, a force transducer, and combination of any thereof. The compressible member 94 translates the force from the drive member 19 and motor 31 to the sensor 100 with a minimal loss of acoustic and/or frictional energy. The compressible member 94 is movable between a first, uncompressed position (shown in FIG. 7) and a second, at least partially compressed position (not shown), wherein the proximal end 102 of compressible member 94 is moved toward the distal end 104 due to the urging force imparted by the drive member 19 driven by the motor 31. Compression of the compressible member 94 between the first, uncompressed position and the second, at least partially compressed position requires the drive member 19 to move in the same manner as during delivery of fluid from a corresponding syringe 12. Rate of compression of the compressible member 94 due to the movement of the drive member 19 may be varied by varying the rate at which the drive member 19 is advanced to simulate different flow rates. The compressible member 94 may be resilient, wherein the compressible member 94 reverts to the uncompressed position from the compressed position after the urging force imparted by the drive member 19 is removed, such as due to retraction of the drive member 19. In some examples, the compressible member 94 may be one or more mechanical springs. In other examples, the compressible member 94 may be a spring, a plurality of springs, a pneumatic compression cell, a hydraulic compression cell, a compressible foam, an elastomer, a compressible rod, such as a rod made from a compressible elastomeric material, a material that changes at least one measurable property, for example electrical resistivity, when compressed, and combinations of any thereof. In certain embodiments, an incompressible engagement may be used between the drive member 19 and the sensor 100 such that the force translates directly from the drive member 19 to the sensor 100 and feeds back into the controller for calibration. According to certain embodiments, the system may use motor current translation (PID) to determine pressure, which may vary with motor speed. In other embodiments, one or more of a strain gauge, a force sensor may be used to determine applied force. The compressible member 94 may provide sufficient stroke length for different motor speeds.

Figure 9:
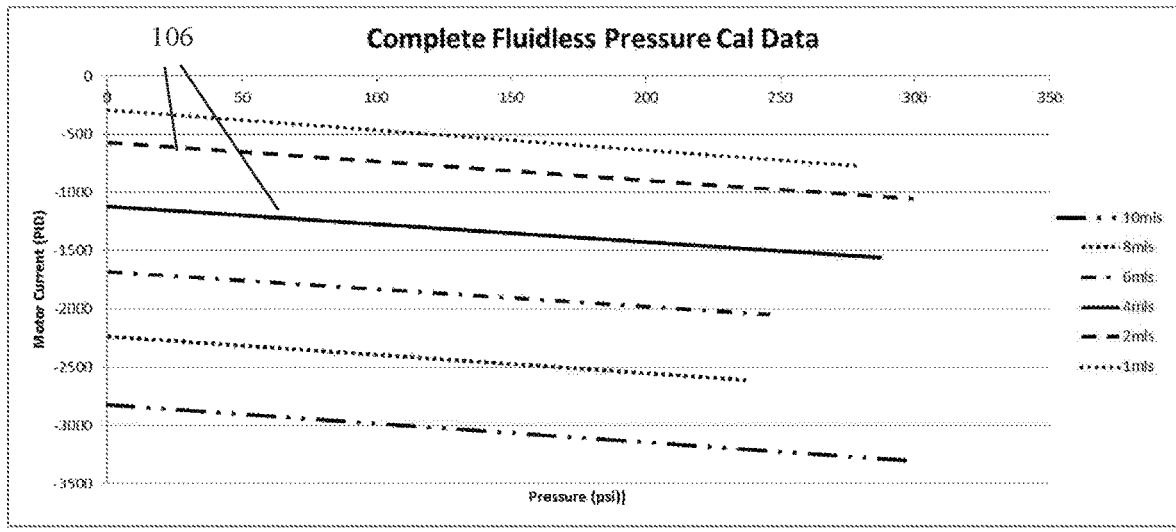
FIG. 9 is a two-dimensional graph showing a correlation between real pressure values with an output of a piston of a fluid injector.
Figure 10:
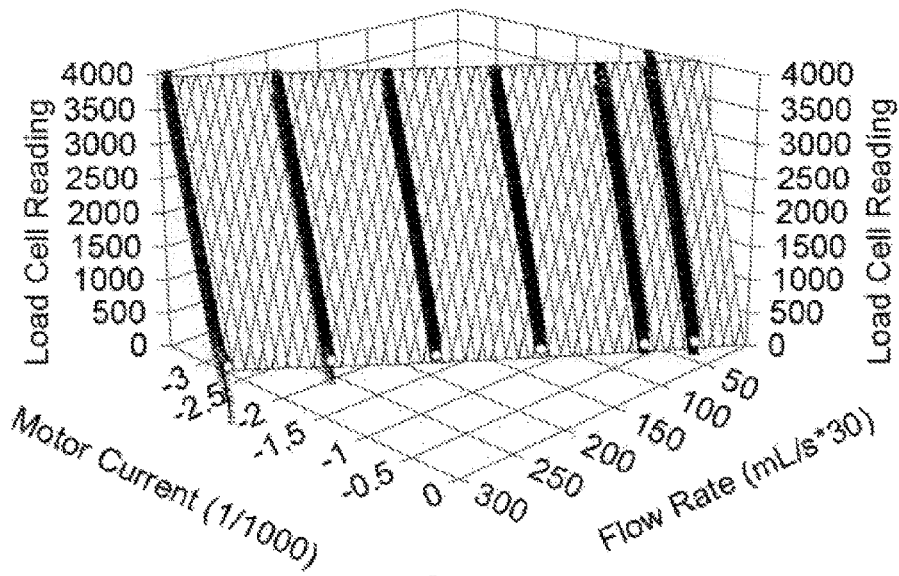
FIG. 10 is a three-dimensional graph showing a correlation between real pressure values, an output of a piston of a fluid injector, and a flow rate corresponding to the movement of the piston.

With further reference to FIG. 7, the sensor 100 is configured to measure the force that the drive member 19 and the motor 31 impart on the calibration system 80. In some examples, the sensor 100 may be a force gauge or a strain gauge. In other examples, the sensor 100 may comprise a motor that pushes against the distal end 104 of the compressible member 94 based on the force imparted on the proximal end 102 of the compressible member 94 by the drive member 19 and the motor 31. In other examples, the sensor 100 may be an optical force measurement system, wherein the sensor 100 is configured to measure movement of the compressible member 94 (or a portion of the force gauge 100) relative to the housing 82 as the drive member 19 compresses the compressible member 94 from the first, uncompressed position to the second, at least partially compressed position. According to these embodiments, the output from the sensor 100 (i.e., the measured distance of compression) may be sent to a processor, for example by a wired connection 95 or by wireless communication (e.g., WiFi, Bluetooth, or other wireless communication technology) such as a processor associated with the fluid injector 10, an external processor, a hospital information system, or other processor, for a dynamic correlation of the measurement signal to pressure, for example using the modulus of compression for the compressible member 94 and an appropriate conversion algorithm, such as Hooke's Law for a compressible spring. According to other embodiments, the measurement signal of the sensor 100 may be a voltage signal that is sent a processor, described herein to be converted into a force measurement. Based on an input current of the motor 31 and the voltage signal of the sensor 100, a pressure calibration curve 106 (FIG. 9) can be generated with real pressure values correlated to system readings for motor current. With a plurality of pressure calibration curves 106 plotted for varying motor speeds, a three-dimensional surface profile (FIG. 10) can be created to generate a calibration equation to be used for the drive member 19 and motor 31 combination. By monitoring the pressure readings from the calibration system 80 and noting potential deviations from values on the calibration curve 106 or the three-dimensional surface profiles, fault conditions may be determined or predicted and appropriate remediation may be undertaken, such as a service call and repair or replacement of one or more injector system components that may be out of specification.

Having described the calibration system 80, a method of calibrating the pressure output of the fluid injector 10 will now be described according to an embodiment. After connecting the housing 82 of the calibration system 80 to the fluid injector 10, such as by connecting the proximal end 102 of the housing 82 with the syringe port 13 of the fluid injector 10 and/or by engaging the distal end 104 of the housing 82 with the retaining mechanism 57 of the fluid injector 10, the drive member 19 may be driven distally such that the drive member 19 contacts or connects with the drive member engagement portion 96 of the calibration system 80 for the first, uncompressed position of the compressible member 96. After contact, as the drive member 19 may be further driven distally at a set rate using the motor 31, the compressible member 94 is compressed from the first, uncompressed position to a second, at least partially compressed position associated with the applied force by the drive member 19 on the compressible member 94 and the force imparted may be transferred to the sensor 100. The sensor 100 may measure the force imparted by the drive member 19 and the motor 31 and send the measurement data to processor, such as described herein such that the input of the motor 31 can be adjusted based on a calibration curve 106 for each flow rate. The process can be repeated for various rates of movement of the drive member 19 that correspond to various flow rates to generate a three-dimensional calibration equation that calibrates the motor input/pressure output for various flow rates (see FIG. 10). In certain embodiments, the calibration curve may be utilized to adjust motor current or force such that multiple motors in a multi-fluid injector system may impart the accurate pressure to fluid within the syringe during an injection protocol. In various embodiments, the calibration equation or calibration data may be used to monitor injector calibration and highlight trends over time, such as weakening of motor strength or other injector components so that such wear or defect may be corrected before failure. An analysis of accumulated or stored data based on the distance of motor travel relative to the force sensed by the calibration unit may provide an indication of some wear, potential failure, or failure.

Figure 11:
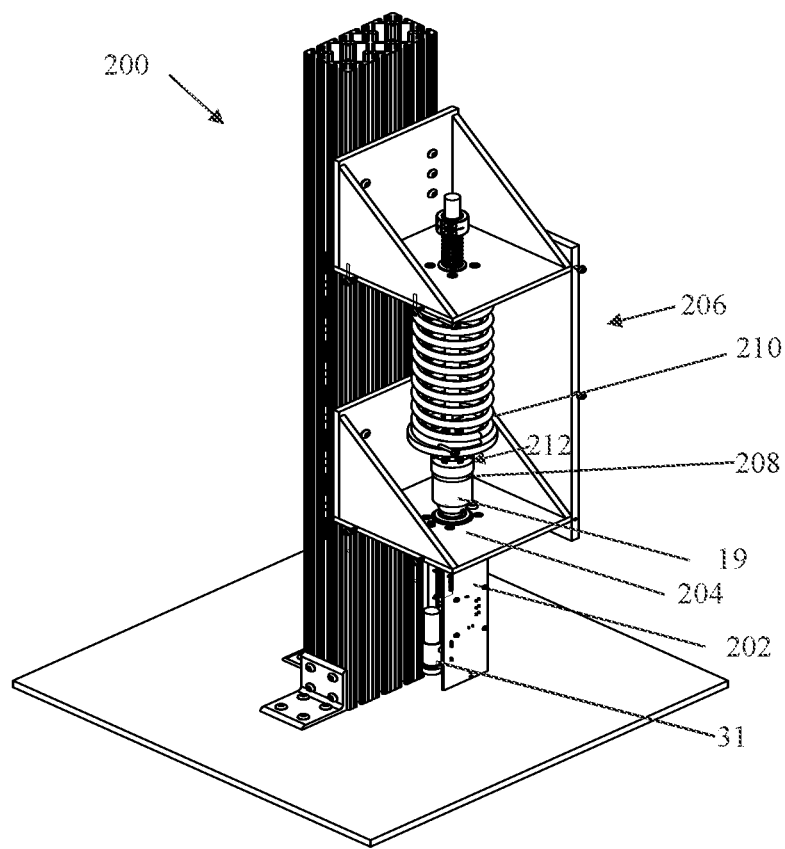
FIG. 11 is a front perspective view of a drive mechanism calibration fixture in accordance with an example of the present disclosure.

With reference to FIG. 11, a calibration fixture 200 is shown in accordance with an example of the present disclosure. The calibration fixture 200 can be used to test a drive mechanism 202 of an injector separately from the injector. In some examples, the calibration fixture 200 is configured for calibrating the pressure output of the drive mechanism 202 that is removable from the injector (not shown). In this manner, the calibration fixture 200 can be used to test a variety of different drive mechanisms 202 configured for use with a variety of different injectors separate from the injectors themselves. The drive mechanism 202 may comprise a motor 31 and a drive member 19, such as a piston.

With continued reference to FIG. 11, the calibration fixture 200 has a mounting platform 204 for mounting the drive mechanism 202. The mounting platform 204 has an opening (not shown) for receiving at least a portion of the drive mechanism 202, such as the piston 19. In this manner, the drive mechanism 202 may be fixedly mounted to the mounting platform 204 while the piston 19 extends through the opening to engage a force sensor 212. The calibration fixture 200 may have a piston engagement portion 208, a compressible member 210, and a force gauge 212. The piston engagement portion 208 is configured for contacting or connecting with the piston 19.

Figure 12:
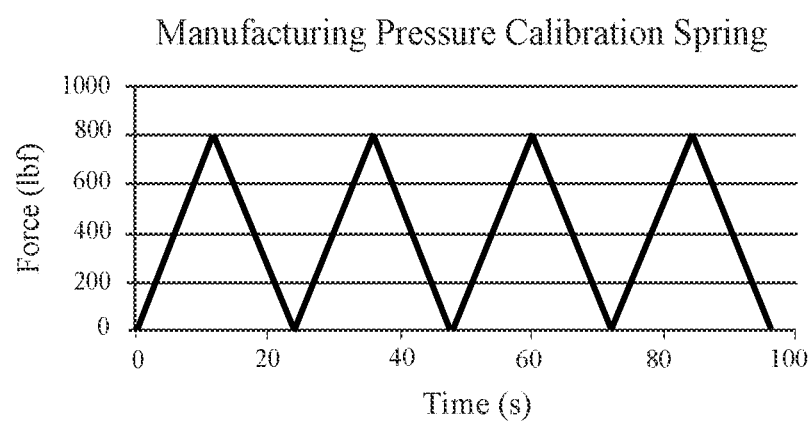
FIG. 12 is a graph showing a pressure calibration curve showing a force as a function of time.

With continued reference to FIG. 11, the compressible member 210, which may be any of the compressible members described herein, translates the force from the drive member 19 and motor 31 to a sensor 212, such as a force gauge, a strain gauge, a force sensor, a load cell, a pressure sensor, a force transducer, and combination of any thereof. The compressible member 210 is movable between a first, uncompressed position and a second, at least partially compressed position due to the urging force imparted by the drive member 19 driven by the motor 31. Compression of the compressible member 210 between the uncompressed position and the at least partially compressed position allows the drive member 19 to move in the same manner as during delivery of fluid from a syringe 12. The compressible member 210 may be compressed by the drive member 19 at a varying force over time (see, FIG. 12) to simulate different flow rates. The compressible member 210 may be resilient, wherein the compressible member 210 reverts to the first, uncompressed position from the compressed second, at least partially position after the urging force imparted by the drive member 19 is removed, such as due to retraction of the drive member 19. In some examples, the compressible member 210 may be a mechanical spring. In certain embodiments, the compressible member 210 has sufficient length to be compressed over the entire stroke of the drive member 19.

With continued reference to FIG. 11, the sensor 212 may be configured to measure the force that the drive member 19 and the motor 31 impart on the calibration fixture 200. A plurality of sensors 212 may be used to provide redundant readings. The motor output, as measured by the sensor 212, can be correlated to a pressure value that would be generated if the drive member 19 was driving a fluid-filled syringe in a manner similar described herein with reference to FIG. 10.

Using the calibration fixture 200, the drive mechanism 202 can be pressure calibrated independently of the injector. In this manner, a defective drive mechanism 202 may be replaced with a new drive mechanism 202 that has been calibrated without causing any additional downtime to the injector due to further pressure calibration of a new drive mechanism.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

What is claimed is:

1. A calibration system for calibrating a pressure output of a drive member of a fluid injector, the calibration system comprising:
    a housing configured for connecting to the fluid injector;
    a drive member engagement portion configured for contacting a drive member of the fluid injector;
    a compressible member connected at its proximal end to the drive member engagement portion, wherein the compressible member is compressed with movement of the drive member of the fluid injector in a distal direction between a first, uncompressed position and a second, at least partially compressed position; and
    a sensor connected to the compressible member, wherein the sensor is configured for measuring a force imparted by the drive member when the compressible member is in the second, at least partially compressed position.

2. The calibration system of claim 1, wherein the sensor is selected from a group consisting of a strain gauge, a force sensor, a load cell, a pressure sensor, a force transducer, and combination of any thereof.

3. The calibration system of claim 2, wherein the sensor comprises a strain gauge.

4. The calibration system of claim 2, wherein the sensor comprises a force sensor.

5. The calibration system of claim 1, wherein the compressible member is selected from a group consisting of a spring, a plurality of springs, a pneumatic compression cell, a hydraulic compression cell, a compressible foam, an elastomer, and combinations of any thereof.

6. The calibration system of claim 5, wherein the compressible member is a spring.

7. The calibration system of claim 1, wherein the sensor is in wired or wireless communication with a processor and an output of the sensor is transmitted to the processor.

8. The calibration system of claim 1, wherein an output of the sensor is used to calibrate an input to one or more of a motor, the drive member, a ball screw in mechanical communication with the motor and the drive member, a frictional component from a disposable fluid delivery reservoir, and other compressible mechanical components.

9. The calibration system of claim 1, wherein an output of the sensor is used to generate a calibration curve for calibrating a pressure output of the drive member of the fluid injector.

10. The calibration system of claim 9, wherein the calibration curve is utilized to determine or predict a fault condition.

11. A calibration system for calibrating a pressure output of a drive member of a fluid injector, the calibration system comprising:
    a housing configured for connecting to the fluid injector;
    a drive member engagement portion configured for contacting a drive member of the fluid injector;
    a compressible member having a known modulus of compression connected at its proximal end to the drive member engagement portion, wherein the compressible member is compressed with movement of the drive member of the fluid injector in a distal direction between a first, uncompressed position and a second, at least partially compressed position; and
    a sensor connected to the compressible member, wherein the sensor is configured for measuring a displacement of the drive member when the compressible member is in the second, at least partially compressed position.

12. The calibration system of claim 11, wherein the compressible member is selected from a group consisting of a spring, a plurality of springs, a pneumatic compression cell, a hydraulic compression cell, a compressible foam, an elastomer, and combinations of any thereof.

13. The calibration system of claim 12, wherein the compressible member is a spring.

14. The calibration system of claim 11, wherein the sensor is in wired or wireless communication with a processor and an output of the sensor is transmitted to the processor.

15. The calibration system of claim 14, wherein the processor determines the pressure output of the fluid injector from the output of the sensor and the modulus of compression of the compressible member.

16. The calibration system of claim 11, wherein an output of the sensor is used to generate a calibration curve for calibrating the pressure output of a drive member of the fluid injector.

17. The calibration system of claim 16, wherein the calibration curve is utilized to determine a fault condition.

18. A method of calibrating a pressure output of a drive member of a fluid injector, the method comprising:
    connecting a calibration system to the fluid injector, the calibration system comprising:
        a housing configured for connecting to the fluid injector;
        a drive member engagement portion configured for contacting a drive member of the fluid injector;
        a compressible member having a known modulus of compression connected at its proximal end to the drive member engagement portion, wherein the compressible member is compressed with movement of the drive member of the fluid injector in a distal direction between a first, uncompressed position and a second, at least partially compressed position; and
        a sensor connected to the compressible member, wherein the sensor is configured for measuring one of a force imparted by the drive member and a displacement of the drive member when the compressible member is in the second, at least partially compressed position;
    contacting a drive member of the fluid injector with the drive member engagement portion of the calibration system;
    driving a motor of the fluid injector to move the drive member and compress the compressible member from the first, uncompressed position to the second, at least partially compressed position; and
    generating a measurement signal by the sensor based on the force imparted on the compressible member by the drive member or the displacement of the drive member when the compressible member is in the second, at least partially compressed position.

19. The method of claim 18, further comprising sending the measurement signal to a processor to calibrate a pressure output of the drive member based on the measurement signal.

20. The method of claim 19, further comprising generating a calibration curve for the pressure output of the drive member.

* * * * *

UNITED STATES PATENT AND TRADEMARK OFFICE
CERTIFICATE OF CORRECTION

PATENT NO. : 11,598,664 B2
APPLICATION NO. : 16/621784
DATED : March 7, 2023
INVENTOR(S) : McDermott et al.

Page 1 of 1

It is certified that error appears in the above-identified patent and that said Letters Patent is hereby corrected as shown below:

In the Specification

In Column 3, Line 57, delete "the a force" and insert -- the force --, therefor.
In Column 5, Line 66, delete "the a force" and insert -- the force --, therefor.
In Column 9, Line 58, delete "an a drive" and insert -- a drive --, therefor.
In Column 11, Line 20, delete "shown" and insert -- shows --, therefor.
In Column 11, Line 63, delete "the a force" and insert -- the force --, therefor.
In Column 12, Line 52, delete "volume" and insert -- volume of --, therefor.
In Column 12, Line 59, delete "volume" and insert -- volume of --, therefor.
In Column 12, Line 61, delete "volume" and insert -- volume of --, therefor.
In Column 14, Lines 33-34, delete "described in described in" and insert -- described in --, therefor.
In Column 14, Line 59, delete "the a drive" and insert -- the drive --, therefor.
In Column 19, Line 5, delete "sent" and insert -- sent to --, therefor.

Signed and Sealed this
Twenty-fifth Day of July, 2023

Katherine Kelly Vidal
*Director of the United States Patent and Trademark Office*